(12) United States Patent
Hamachi et al.

(10) Patent No.: US 12,297,308 B2
(45) Date of Patent: May 13, 2025

(54) ETHANOL

(71) Applicant: SEKISUI CHEMICAL CO., LTD., Osaka (JP)

(72) Inventors: Kokoro Hamachi, Tsukuba (JP); Noritoshi Yagihashi, Tsukuba (JP); Haruka Nishiyama, Tsukuba (JP); Kazuto Natsuyama, Tsukuba (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 18/387,137

(22) Filed: Nov. 6, 2023

(65) Prior Publication Data

US 2024/0141088 A1 May 2, 2024

Related U.S. Application Data

(62) Division of application No. 17/426,019, filed as application No. PCT/JP2020/003026 on Jan. 28, 2020, now abandoned.

(30) Foreign Application Priority Data

Jan. 28, 2019 (JP) ................................. 2019-012564
Jan. 28, 2019 (JP) ................................. 2019-012568

(Continued)

(51) Int. Cl.
*C08F 236/10* (2006.01)
*C07C 1/24* (2006.01)
(Continued)

(52) U.S. Cl.
CPC .............. *C08F 236/10* (2013.01); *C07C 1/24* (2013.01); *C07C 29/80* (2013.01); *C07C 31/08* (2013.01);
(Continued)

(58) Field of Classification Search
CPC ........ C08F 236/10; C08F 36/06; C08F 36/08; C08F 236/06; C08F 36/04; C08F 212/06;
(Continued)

(56) References Cited

U.S. PATENT DOCUMENTS 5,258,293 A 11/1993 Lynd et al.
6,136,577 A * 10/2000 Gaddy ................... C12M 43/02
435/163

(Continued)

FOREIGN PATENT DOCUMENTS

CN 107001177 A 8/2017
EP 3 246 301 A1 11/2017
(Continued)

OTHER PUBLICATIONS

Extended European Search Report dated Feb. 28, 2022 in European Application No. 20748171.4.

(Continued)

*Primary Examiner* — Cephia D Toomer
(74) *Attorney, Agent, or Firm* — Sughrue Mion, PLLC

(57) ABSTRACT

The present disclosure provides a novel and practical alcohol and derivatives thereof which have more industrial value than existing petrochemical raw materials. The present disclosure further provides ethanol, characterized in that a peak in gas chromatography measured by gas chromatograph mass spectrometry (GC/MS) has at least one peak with a retention time selected from (A) a peak of 5 minutes 25 seconds to 5 minutes 35 seconds and two peaks of 2 minutes 55 seconds to 3 minutes 5 seconds; (B) a peak of 12 minutes 30 seconds to 12 minutes 40 seconds; (C) a peak of 6 minutes 36 seconds to 6 minutes 45 seconds; and (D) a peak of 15 minutes 00 seconds to 15 minutes 15 seconds.

18 Claims, 5 Drawing Sheets

(30) Foreign Application Priority Data

| | | |
|---|---|---|
| Mar. 18, 2019 | (JP) | 2019-050436 |
| Mar. 18, 2019 | (JP) | 2019-050465 |
| Mar. 18, 2019 | (JP) | 2019-050472 |
| Mar. 18, 2019 | (JP) | 2019-050474 |
| Mar. 18, 2019 | (JP) | 2019-050480 |
| Mar. 18, 2019 | (JP) | 2019-050484 |
| Mar. 18, 2019 | (JP) | 2019-050489 |
| Jun. 25, 2019 | (JP) | 2019-117720 |
| Jun. 25, 2019 | (JP) | 2019-117745 |
| Jun. 25, 2019 | (JP) | 2019-117749 |
| Jun. 25, 2019 | (JP) | 2019-117754 |
| Jul. 5, 2019 | (JP) | 2019-126455 |

(51) Int. Cl.

| | |
|---|---|
| *C07C 29/80* | (2006.01) |
| *C07C 31/08* | (2006.01) |
| *C07C 67/08* | (2006.01) |
| *C08C 19/00* | (2006.01) |
| *C08J 3/20* | (2006.01) |
| *C10J 3/72* | (2006.01) |
| *C10K 1/00* | (2006.01) |
| *C10L 1/02* | (2006.01) |
| *C12N 1/20* | (2006.01) |
| *C12P 7/06* | (2006.01) |
| *C12P 7/08* | (2006.01) |
| *B60C 1/00* | (2006.01) |
| *C08F 36/06* | (2006.01) |
| *C08F 36/08* | (2006.01) |
| *C12R 1/145* | (2006.01) |

(52) U.S. Cl.
CPC ............ *C07C 67/08* (2013.01); *C08C 19/00* (2013.01); *C08J 3/203* (2013.01); *C10J 3/72* (2013.01); *C10K 1/005* (2013.01); *C10L 1/02* (2013.01); *C12N 1/20* (2013.01); *C12P 7/06* (2013.01); *C12P 7/065* (2013.01); *C12P 7/08* (2013.01); *B60C 1/0016* (2013.01); *B60C 1/0025* (2013.01); *B60C 1/0041* (2013.01); *B60C 2001/005* (2013.01); *C08F 36/06* (2013.01); *C08F 36/08* (2013.01); *C08J 2309/06* (2013.01); *C10J 2300/0946* (2013.01); *C10J 2300/1665* (2013.01); *C10L 2290/26* (2013.01); *C12R 2001/145* (2021.05)

(58) Field of Classification Search
CPC ......... C08F 236/04; C07C 1/24; C07C 29/80; C07C 31/08; C07C 67/08; C07C 2521/06; C07C 2523/06; C07C 1/20; C08C 19/00; C08J 3/203; C08J 2309/06; C10J 3/72; C10J 2300/0946; C10J 2300/1665; C10K 1/005; C10K 1/32; C10L 1/02; C10L 2290/26; C12N 1/20; C12N 1/00; C12P 7/06; C12P 7/065; C12P 7/08; B60C 1/0016; B60C 1/0025; B60C 1/0041; B60C 2001/005; C12R 2001/145; Y02C 20/40; Y02E 50/10; B01D 53/047; B01J 20/18; B01J 20/34; C01B 3/56; C01B 39/22; C07B 61/00; C08K 3/013; C08L 9/00; C08L 101/00; C12M 1/00
See application file for complete search history.

(56) References Cited

U.S. PATENT DOCUMENTS

| | | |
|---|---|---|
| 2004/0181101 A1 | 9/2004 | Fanselow et al. |
| 2011/0136962 A1 | 6/2011 | Hattori et al. |
| 2012/0052541 A1 | 3/2012 | Oakley |
| 2017/0260552 A1 | 9/2017 | Haas et al. |
| 2022/0204997 A1 | 6/2022 | Hamachi et al. |

FOREIGN PATENT DOCUMENTS

| | | | |
|---|---|---|---|
| JP | 2011-512869 A | 4/2011 | |
| JP | 2011-514236 A | 5/2011 | |
| JP | 2012-97163 A | 5/2012 | |
| JP | 2012-205530 A | 10/2012 | |
| JP | 2013-49023 A | 3/2013 | |
| JP | 2013-515482 A | 5/2013 | |
| JP | 2014-518089 A | 7/2014 | |
| JP | 2015-42711 A | 3/2015 | |
| JP | 2016-059296 A | 4/2016 | |
| JP | 2016-524927 A | 8/2016 | |
| JP | 2017-2168 A | 1/2017 | |
| JP | 2018-058042 A | 4/2018 | |
| JP | 2018-070465 A | 5/2018 | |
| JP | 2019-88240 A | 6/2019 | |
| WO | WO-2009112334 A1 * | 9/2009 | ............ C12P 7/065 |
| WO | 2010/082202 A2 | 7/2010 | |
| WO | 2015/037710 A1 | 3/2015 | |
| WO | 2015/058011 A1 | 4/2015 | |
| WO | 2017/221987 A1 | 12/2017 | |

OTHER PUBLICATIONS

Notification of Reasons for Refusal dated Apr. 11, 2023 from the Japanese Patent Office in application No. 2019-117720.
Office Action issued Jan. 6, 2023 in Japanese Application No. 2019-012564.
Office Action issued Jan. 6, 2023 in Japanese Application No. 2019-050489.
Dyah Styarini et al., "Determination of organic impurities in lignocellulosic bioethanol product by GC-FID", Energy Procedia, vol. 32, 2013, pp. 153-159 (5 pages total).
Notification of Reasons for Refusal dated Apr. 11, 2023 from the Japanese Patent Office in application No. 2019-117745.
Office Action issued Jan. 6, 2023 in Japanese Application No. 2019-050474.
Tatiana Dillenburg Saint'Pierre et al., "The development of a method for the determination of trace elements in fuel alcohol by electrothermal vaporization-inductively coupled plasma mass spectrometry using external calibration," Spectrochimica Acta Part B, vol. 60, pp. 605-613 (9 pages total).
Notification of Reasons for Refusal dated Apr. 11, 2023 from the Japanese Patent Office in application No. 2019-117754.
International Search Report of PCT/JP2020/003026 dated Apr. 14, 2020 [PCT/ISA/210].
Communication dated Aug. 12, 2021 issued by the International Bureau in International Application No. PCT/JP2020/003026.
Office Action issued Jan. 6, 2023 in Japanese Application No. 2019-050484.
Office Action issued Jan. 6, 2023 in Japanese Application No. 2019-050472.
Jamal Abrini et al., "*Clostridium autoethanogenum*, sp. nov., an anaerobic bacterium that produces ethanol from carbon monoxide", Archives of Microbiology, 1994, vol. 161, pp. 345-351 (7 pages total).
Office Action issued Feb. 17, 2023 in European Application No. 20 749 002.0.
Notification of Reasons for Refusal dated Apr. 11, 2023 from the Japanese Patent Office in application No. 2019-117749.
"SLB IL (i-series) Capillary GC Columns", Sigma-Aldrich, SUPELCO, 2016, XP055892831, Retrieved from: URL: <https://www.sigmaaldrich.com/deepweb/assets/sigmaaldrich/marketing/global/documents/343/210/T416028-slb-iseries-capillary-gc.pdf> (6 pages total).
Deshun Xu et al., "The effects of syngas impurities on syngas fermentation to liquid fuels", Biomass and Bioenergy, 2011, vol. 35, No. 7, pp. 2690-2696 (7 pages total).
Office Action issued Jan. 6, 2023 in Japanese Application No. 2019-050480.

(56) References Cited

OTHER PUBLICATIONS

Office Action issued Feb. 14, 2023 in Japanese Application No. 2019-050436.
Chinese Office Action issued Jul. 7, 2023 in Application No. 202080011053.7.
Communication issued Feb. 17, 2023 in European Application No. 20 749 002.0.
Office Action issued Oct. 6, 2023 in Japanese Application No. 2019-117745.
Office Action issued Oct. 10, 2023 in Japanese Application No. 2019-117720.
Office Action issued Oct. 10, 2023 in Japanese Application No. 2019-117749.
Office Action issued Oct. 10, 2023 in Japanese Application No. 2019-117754.
Japanese Office Action issued Sep. 5, 2023 in Application No. 2020-016613.
United States Office Action issued Sep. 27, 2023 in U.S. Appl. No. 17/422,654.
Carlos Sanchez et at., "Metal and metalloid determination in bioethanol through inductively coupled plasma-optical emission spectroscopy", Spectrochimica Acta. Part B, 2016, vol. 115, pp. 16-22 (7 pages total).
"Margarita mix", Brand: NINA'S, Aug. 9, 2018, Food Data Central (4 pages total).
Trees De Baerdemaeker, et al., " Bimetallic Zn and Hf on Silica Catalysts for the Conversion of Ethanol to 1,3-Butadiene" , ACS Catalysis, 2015, vol. 5, No. 6, pp. 3393-3397 (15 pages).
United States Office Action dated Jan. 16, 2024 in U.S. Appl. No. 17/297,770.
Chinese Office Action dated Nov. 29, 2023 in App. No. 202080011240.5.
Office Action issued Jul. 9, 2024 in Chinese Application No. 202080011240.5.
Office Action issued Jul. 12, 2024 in Japanese Application No. 2023-133155.
Office Action issued Jul. 12, 2024 in Japanese Application No. 2023-133156.
Office Action issued Jul. 12, 2024 in Japanese Application No. 2023-133158.
Office Action issued Jul. 12, 2024 in Japanese Application No. 2023-133159.
Office Action issued Jul. 30, 2024 in Japanese Application No. 2020-016613.
Decision of Refusal dated Apr. 19, 2024, issued in Japanese Application No. 2019-117720.
Decision of Refusal dated Apr. 19, 2024, issued in Japanese Application No. 2019-117749.
Decision of Refusal dated Apr. 19, 2024, issued in Japanese Application No. 2019-117754.
Notice of Termination of Reconsideration by Examiners before Appeal Proceedings dated May 7, 2024, issued in Japanese Application No. 2019-117745.
Reconsideration Report by Examiner before Appeal drafted Apr. 23, 2024, issued in Japanese Application No. 2019-117745.
U.S. Office Action dated Apr. 4, 2024, issued in U.S. Appl. No. 17/422,654.
Fredrik Aldaeus et al., "Prediction of retention times of polycyclic aromatic hydrocarbons and n-alkanes in temperature-programmed gas chromatography", Anal Bioanal Chem, 2007, vol. 389, pp. 941-950 (10 pages).
The Interstate Technology & Regulatory Council (ITRC) Petroleum Vapor Intrusion Team, "Appendix C" of "Petroleum Vapor Intrusion: Fundamentals of Screening, Investigation, and Management", Oct. 2014, pp. 129-134 (9 pages).
Fabio Monticelli et al., "Another case of diethyl ether intoxication? A case report focusing on toxicological analysis", Legal Medicine, 2011, vol. 13, pp. 254-258 (5 pages).
Jana Stavova et al., "Method development for the characterization of biofuel intermediate products using gas chromatography with simultaneous mass spectrometric and flame ionization detections", Journal of Chromatography A, 2012, vol. 1224, pp. 79-88 (10 pages).
"Alkyl", Wikipedia, Archived via The Wayback Machine, 2017, p. 1-4 (4 pages) URL: https://web.archive.org/web/20170325081756/ https://en.wikipedia.org/wiki/Alkyl_group.
Notice of Reasons for Refusal dated Jun. 21, 2024 in Japanese Application No. 2023-121066.
Notice of Reasons for Refusal dated Jun. 21, 2024 in Japanese Application No. 2023-121071.
Notice of Reasons for Refusal dated Jun. 21, 2024 in Japanese Application No. 2023-121080.
Communication issued Dec. 21, 2024 in Chinese Application No. 202080011240.5.
Communication dated Oct. 8, 2024, issued in Japanese Application No. 2019-117720.
Communication dated Oct. 8, 2024, issued in Japanese Application No. 2019-117749.
Communication dated Oct. 8, 2024, issued in Japanese Application No. 2019-117754.
Communication pursuant to Rule 114(2) EPC dated Mar. 21, 2025 including observations filed by a Third Party to the EP Application No.20749002.0.
Communication to Rule 114(2) EPC dated Mar. 21, 2025 including observations filed by a Third Party to the EP Application No.20748171.4.

* cited by examiner

ETHANOL

CROSS-REFERENCE TO RELATED APPLICATIONS

This application is a divisional of application Ser. No. 17/426,019 filed Jul. 28, 2021, which is a National Stage of International Application No. PCT/JP2020/003026, filed Jan. 28, 2020, claiming priority to Japanese Patent Application Nos. 2019-012564 and 2019-012568, filed Jan. 28, 2019; Japanese Patent Application Nos. 2019-050436, 2019-050465, 2019-050472, 2019-050474, 2019-050480, 2019-050484 and 2019-050489, filed Mar. 18, 2019; Japanese Patent Application Nos. 2019-117720, 2019-117745, 2019-117749, and 2019-117754, filed Jun. 25, 2019; and Japanese Patent Application No. 2019-126455, filed Jul. 5, 2019; the entire contents of which are incorporated herein by reference.

BACKGROUND OF THE INVENTION

The present invention relates to ethanol and, more particularly, to ethanol in which the content of specific trace components is adjusted, especially to novel resource recycling type ethanol using a gas comprising carbon monoxide and hydrogen as a substrate, which is not derived from conventional petroleum resources or biomass resources.

BACKGROUND ART

Petrochemical products are used in various parts of our lives. On the other hand, because they are familiar products, they cause various environmental problems due to mass production and mass consumption, which is a major problem on a global scale. For example, polyethylene and polyvinyl chloride, which are representative products of petrochemical industry, are consumed in large quantities and disposed of, and these wastes are a major cause of environmental pollution. In addition, concerns about the depletion of fossil fuel resources and global environmental issues such as the increase of carbon dioxide in the atmosphere have been discussed when petrochemical industry products are mass-produced.

In view of increasing awareness of such environmental problems on a global scale, methods for producing various organic substances from raw materials other than naphtha, which is a raw material for petrochemical products, have recently been studied. For example, attention has been drawn to a method for producing bioethanol from edible raw materials such as corn by a sugar fermentation method. However, it has been pointed out that such a sugar fermentation method using edible raw materials uses the limited farmland area for production other than food, which leads to escalation in food prices.

In order to solve this problem, the use of non-edible raw materials that have conventionally been disposed of has also been considered. Specifically, there have been proposed methods for producing alcohols by a fermentation method using waste wood, cellulose derived from waste paper, or the like as non-edible raw materials, and methods for producing alcohols by gasifying biomass raw materials as described above and using a catalyst from synthetic gas, but the current situation is that these methods have not yet been put into practical use. Furthermore, even if various petrochemical products can be produced from these de-petrochemical raw materials, they will eventually become waste plastics that do not decompose naturally, and therefore they are not effective as a fundamental solution to environmental problems.

Currently, combustible waste disposed of in Japan reaches to about 60,000,000 tons/year. The amount of energy is equivalent to about 2 hundred trillion kilocalories, which is much more than that of naphtha used as a raw material for plastics in Japan, and it can be said that these wastes are also heavy resources. If these waste resources can be converted into petrochemical products, it will be possible to realize an ultimate resource recycling society that does not rely on petroleum resources. In view of the above, Patent Documents 1 and 2 disclose techniques for producing a synthetic gas (a gas mainly composed of CO and $H_2$) from waste and producing ethanol from the synthetic gas by a fermentation process.

However, as also pointed out in Patent Document 3, synthetic gas produced from waste contains a wide variety of impurities that have not been revealed, and some of them are toxic to microorganisms, so that the productivity has become a large problem in producing alcohol from synthetic gas by microbial fermentation. Also, alcohol obtained by microbial fermentation of synthetic gas contains various components derived from impurities in the synthetic gas, and these components cannot be completely removed by purification treatment such as distillation. Therefore, the development of derivatives from alcohol obtained by microbial fermentation of synthetic gas has been a major technical problem.

PRIOR ART DOCUMENTS

Patent Documents

Patent Document 1: Japanese Patent Application Laid-Open Publication No. 2016-059296
Patent Document 2: International Publication No. WO2015-037710
Patent Document 3: Japanese Patent Application Laid-Open Publication No. 2018-058042

SUMMARY OF THE INVENTION

Problems to be Solved by the Invention

According to examination by the present inventors, for example, C2 raw material represented by conventional ethanol is known as a starting material for various chemical products, but as described above, it has been found that alcohol produced from resources other than petroleum resources or biomass resources (recycling type resources) contains various unknown substances in small amounts unlike chemical raw materials derived from naphtha. However, in the prior art, the properties of the substances are also unknown, and thus no conventional studies were carried out on whether all the substances should be removed or only specific substances should be removed. Therefore, even if the above-mentioned patent documents propose alcohols produced from recyclable resources, there is still room for technical improvement in order to put the alcohols into practical use.

On the other hand, according to the above-mentioned documents, although general fermentation and distillation methods, optimum composition of synthetic gas, and the like are disclosed, the details of the process, etc. are not described, and even the obtained alcohol substance is not specified.

Accordingly, the present invention has been made in view of such background art, and the problem is to provide a practically novel alcohol having an industrial value more than that of existing petrochemical raw materials, and derivatives thereof.

Means for Solving the Problem

As a result of intensive studies to solve the above-mentioned problem, it has been found that it is possible to specify a wide variety of trace substances contained in alcohol produced from recycling type resources, and further to control the content within a specific range by a novel production method, and that various derived products thereof exhibit superior effect compared to existing petrochemical derived alcohols. For example, in the process of synthesizing butadiene from ethanol, it has been found that the ethanol conversion rate was improved compared to the case where the conventional ethanol derived from petrochemical is used, and an alcohol of a practical level equivalent to or higher than that of the alcohol derived from petrochemical is obtained, thereby arriving at the present invention.

More specifically, when ethanol is produced from a gas substrate containing carbon monoxide and hydrogen using waste as the carbon source, it was found that the conversion rate of ethanol is improved when butadiene is synthesized from the ethanol, and when the reason for this was examined in details, it was found that ethanol derived from a recycling type resource using a gas comprising carbon monoxide and hydrogen as the substrate has a characteristic peak in gas chromatography measured by gas chromatograph mass spectrometry that cannot be seen from ethanol derived from fossil fuels. The present invention is based on such finding.

That is, the present invention includes the following features.

[1] Ethanol wherein a peak in gas chromatography measured by gas chromatograph mass spectrometry (GC/MS) has at least one peak with a retention time selected from the group consisting of the following (A) to (D):
  (A) a peak of 5 minutes 25 seconds to 5 minutes 35 seconds and two peaks of 2 minutes 55 seconds to 3 minutes 5 seconds;
  (B) a peak of 12 minutes 30 seconds to 12 minutes 40 seconds;
  (C) a peak of 6 minutes 36 seconds to 6 minutes 45 seconds; and
  (D) a peak of 15 minutes 00 seconds to 15 minutes 15 seconds.

[2] The ethanol according to [1], wherein the peak in the gas chromatography further has a peak with the retention time of 5 minutes 30 seconds to 5 minutes 35 seconds in addition to the peak of (A).

[3] The ethanol according to [1], wherein the peak of (B) is derived from n-tetradecane.

[4] The ethanol according to [3], wherein the concentration of n-tetradecane is 0.01 mg/L or more and 1.0 mg/L or less.

[5] The ethanol according to [1], wherein the peak of (C) is derived from n-decane.

[6] The ethanol according to [5], wherein the concentration of n-decane is between 0.01 mg/L and 1.0 mg/L.

[7] The ethanol according to [1], wherein the peak of (D) is derived from n-hexadecane.

[8] The ethanol according to [7], wherein the concentration of n-hexadecane is 0.01 mg/L or more and 1.0 mg/L or less.

[9] The ethanol according to any one of [1] to [8], wherein a substrate is a gas containing carbon monoxide and hydrogen.

[10] The ethanol according to [9], wherein the gas containing carbon monoxide and hydrogen is derived from waste.

[11] The ethanol according to any one of [1] to [10], wherein the ethanol is derived from microbial fermentation.

[12] A method for manufacturing ethanol, comprising:
  a step of converting a carbon source into a synthetic gas comprising carbon monoxide and hydrogen;
  a microbial fermentation step of supplying the synthetic gas comprising carbon monoxide and hydrogen to a microbial fermentation tank to obtain an ethanol-containing liquid by microbial fermentation;
  a separation step of separating the ethanol-containing liquid into a liquid or solid component containing microorganisms and a gas component containing ethanol;
  a liquefaction step of condensing and liquefying the gas component;
  a purification step of purifying ethanol from the liquid obtained in the liquefaction step;
  wherein the purified ethanol is characterized in that a peak in gas chromatography measured by gas chromatograph mass spectrometry (GC/MS) has at least one peak with a retention time selected from the group consisting of the following (A) to (D):
  (A) a peak of 5 minutes 25 seconds to 5 minutes 35 seconds and two peaks of 2 minutes 55 seconds to 3 minutes 5 seconds;
  (B) a peak of 12 minutes 30 seconds to 12 minutes 40 seconds;
  (C) a peak of 6 minutes 36 seconds to 6 minutes 45 seconds; and
  (D) a peak of 15 minutes 00 seconds to 15 minutes 15 seconds.

[13] The method according to [12] further comprising the step of purifying the synthetic gas.

[14] The method according to [12] or [13], wherein the carbon source is derived from waste.

[15] The ethanol of any one of [1] to [11], used in a chemical product, a polymer raw material, or a fuel.

[16] A chemical product using ethanol according to any one of [1] to [11] as a raw material.

[17] A fuel comprising ethanol according to any one of [1] to [11] and/or ethyl-t-butyl ether using ethanol according to any one of [1] to [6] as a raw material.

[18] A polymer raw material using ethanol according to any one of [1] to [11] as a raw material.

[19] The polymer raw material according to [18], selected from the group consisting of ethylene, propylene, butadiene, ethyl acetate, isobutene, methyl(meth)acrylate, acrylic acid, aminohexanoic acid, and diethyl carbonate.

[20] A polymer comprising the polymer raw material according to [18] or [19].

[21] A molded article comprising the polymer according to [20].

Effect of the Invention

According to the present invention, by using ethanol having extremely small amounts of specific organic components, various different effects can be obtained compared with commercial ethanol for industrial use. For example, according to the present invention, it is possible to improve the ethanol conversion rate when butadiene is synthesized using ethanol as a raw material, to improve the reaction rate when a carboxylic acid ester is synthesized by adding ethanol to a carboxylic acid, and to improve the combustion efficiency when ethanol is used as a fuel. In addition, even in the case of existing alcohols, it is expected that the same effect can be obtained by adding specific amounts of organic components.

The ethanol according to the present invention can be used as a raw material for producing, for example, butadiene, ethylene, propylene, isobutene, acetaldehyde, acetic acid, ethyl acetate, methyl(meth)acrylate, ethyl-t-butyl ether ethylene glycol, ester composition, polyester, acrylic acid, aminohexanoic acid, diethyl carbonate, polyethylene (PE), polyethylene terephthalate (PET), polypropylene (PP), polyisobutylene, polymethylmethacrylate (PMMA), ethylene propylene diene rubber (EPDM), polybutylene terephthalate (PBT), polyethylene furanoate (PEF), polyurethane (PU), and the like. The ethanol according to the present invention can be used in various purposes of chemical products such as cosmetics, perfumes, fuels, antifreeze solutions, bactericides, disinfectants, cleaners, mold removers, detergents, shampoo, soaps, antiperspirants, face wash sheets, solvents, coatings, adhesives, diluents, food additives, and the like.

MODE FOR CARRYING OUT THE INVENTION

Figure 1A:
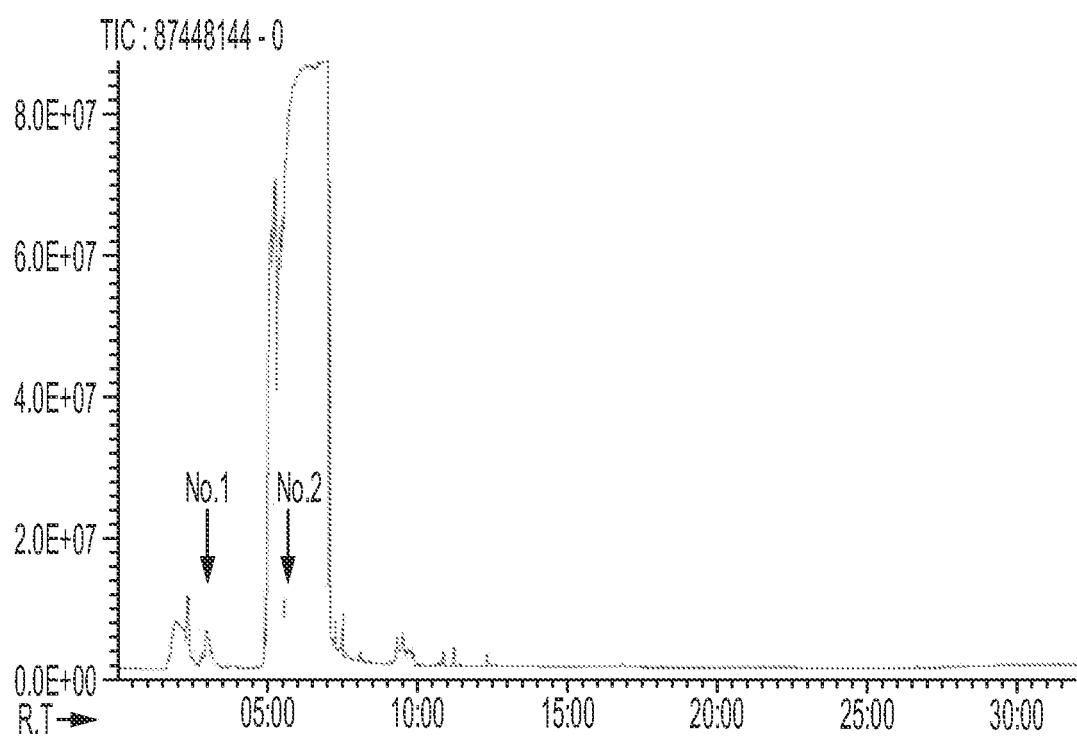
FIG. 1A is a gas chromatogram of ethanol used in Example A1.

One example of a preferred embodiment of the present invention will be described below. However, the following embodiment is an example for describing the present invention, and the present invention shall not be limited to the following embodiment.

Definition

In the present invention, the term "ethanol" does not mean pure ethanol as a compound (ethanol represented by the chemical formula: $CH_3CH_2OH$), but means a composition containing water and impurities (impurity components) inevitably contained in ethanol produced through synthesis or purification.

In the present invention, the content of each component such as an inorganic component or an organic component in an alcohol raw material is the amount (mg) of each component per 1 L of alcohol.

<Ethanol>

The ethanol according to the present invention has a peak in gas chromatography measured by gas chromatograph mass spectrometry (GC/MS) has at least one peak with a retention time selected from the group consisting of the following (A) to (D):

(A) a peak of 5 minutes 25 seconds to 5 minutes 35 seconds and two peaks of 2 minutes 55 seconds to 3 minutes 5 seconds;
(B) a peak of 12 minutes 30 seconds to 12 minutes 40 seconds;
(C) a peak of 6 minutes 36 seconds to 6 minutes 45 seconds; and
(D) a peak of 15 minutes 00 seconds to 15 minutes 15 seconds.

The peaks (A) to (D) are obtained by analyzing ethanol by a GC/MS method under the following analysis conditions.

That is, the two peaks of (A) are obtained by analyzing ethanol by a GC/MS method under the following analysis conditions.

<Analysis Conditions of the GC/MS Method>
Column: Capillary column (length 60 m, inner diameter 0.25 mm, film thickness 0.25 μm)
Oven temperature: 40° C., 1 minute→5° C./min→100° C., 10 minutes→10° C./min→250° C., 4 minutes
Sampling time: 5 minutes
Carrier gas: He (3.0 mL/min)

The peaks (B) to (D) are obtained by analyzing ethanol by a GC/MS method under the following analysis conditions.

<Analysis Conditions of the GC/MS Method>
Column: DB-5MS (Length 30 m, Inner Diameter 0.25 mm, Film Thickness 0.25 μm)
Oven temperature: 40° C.→10° C./min→300° C.
Carrier gas: He (1.28 mL/min)
Inlet temperature: 300° C.
Detector temperature: 300° C.
Detector: Flame ionization detector
Injection volume: 1 μL (split ratio 1:20)

Ethanol of 100% purity, that is, ethanol containing no impurities at all, does not have peaks with retention times of 2 minutes 55 seconds to 3 minutes 5 seconds, 12 minutes 30 seconds to 12 minutes 40 seconds, 6 minutes 36 seconds to 6 minutes 45 seconds, and 15 minutes 00 seconds to 15 minutes 15 seconds in a gas chromatograph measured by the GC/MS method under the above conditions. Also, commercially available industrial ethanol derived from fossil fuels does not have peaks with retention times of 2 minutes 55 seconds to 3 minutes 5 seconds, 12 minutes 30 seconds to 12 minutes 40 seconds, 6 minutes 36 seconds to 6 minutes 45 seconds, and 15 minutes 00 seconds to 15 minutes 15 seconds in the gas chromatograph measured by the GC/MS method under the above conditions. Furthermore, ethanol produced by fermentation using biomass materials such as cellulose does not have peaks with retention times of 2 minutes 55 seconds to 3 minutes 5 seconds, 12 minutes 30 seconds to 12 minutes 40 seconds, 6 minutes 36 seconds to 6 minutes 45 seconds, and 15 minutes 00 seconds to 15 minutes 15 seconds. Accordingly, the peaks with retention times of 2 minutes 55 seconds to 3 minutes 5 seconds, 12 minutes 30 seconds to 12 minutes 40 seconds, 6 minutes 36 seconds to 6 minutes 45 seconds, and 15 minutes 00 seconds to 15 minutes 15 seconds is considered to be characteristic of ethanol derived from microbial fermentation using gases containing carbon monoxide and hydrogen as substrates.

Without being bound by theory, ethanol derived from microbial fermentation using a gas containing carbon monoxide and hydrogen as a substrate is considered to contain various trace components other than carbon monoxide and hydrogen in the synthesis gas used in the production process, and it is considered that a substance having a higher boiling point than ethanol, such as an aldehyde compound, is inevitably contained even in the alcohol obtained through a purification process such as distillation. In the present invention, it is considered that by including these unavoidable substances in ethanol, it is possible to improve the ethanol conversion rate when butadiene is synthesized using ethanol as a raw material or to improve the reaction rate when carboxylic acid ester is synthesized by adding ethanol to carboxylic acid.

The peak with a retention time of 12 minutes 30 seconds to 12 minutes 40 seconds is estimated to be derived from n-tetradecane. The content of n-tetradecane is preferably 0.01 mg/L or more, more preferably 0.02 mg/L or more, further preferably 0.03 mg/L or more, further more preferably 0.05 mg/L or more, and preferably 1 mg/L or less, more preferably 0.5 mg/L or less, further preferably 0.2 mg/L or less, and further more preferably 0.1 mg/L or less with respect to the entire ethanol. When the content of n-tetradecane is within the above-mentioned numerical range, it is possible to improve the ethanol conversion rate when butadiene is synthesized using ethanol as a raw material, to improve the reaction rate when carboxylic acid ester is synthesized by adding ethanol to carboxylic acid, or to improve the combustion efficiency when ethanol is used as a fuel.

The peak with a retention time of 6 minutes 36 seconds to 6 minutes 45 seconds is estimated to be derived from n-decane. The content of n-decane is preferably 0.01 mg/L or more, more preferably 0.02 mg/L or more, further preferably 0.03 mg/L or more, further more preferably 0.05 mg/L or more, and preferably 1 mg/L or less, more preferably 0.5 mg/L or less, further preferably 0.2 mg/L or less, and further more preferably 0.1 mg/L or less with respect to the whole ethanol. When the content of n-decane is within the above-mentioned numerical range, it is possible to improve the ethanol conversion rate when butadiene is synthesized using ethanol as a raw material, to improve the reaction rate when carboxylic acid ester is synthesized by adding ethanol to carboxylic acid, or to improve the combustion efficiency when ethanol is used as a fuel.

The peak with a retention time of 15 minutes 00 seconds to 15 minutes 15 seconds is estimated to be derived from n-hexadecane. The content of n-hexadecane relative to the total ethanol is preferably 0.01 mg/L or more, more preferably 0.02 mg/L or more, further preferably 0.03 mg/L or more, further more preferably 0.05 mg/L or more, and preferably 1 mg/L or less, more preferably 0.5 mg/L or less, further preferably 0.2 mg/L or less, and further more preferably 0.1 mg/L or less. When the content of n-decane is within the above-mentioned numerical range, it is possible to improve the ethanol conversion rate when butadiene is synthesized using ethanol as a raw material, to improve the reaction rate when carboxylic acid ester is synthesized by adding ethanol to carboxylic acid, or to improve the combustion efficiency when ethanol is used as a fuel.

It is preferable that ethanol derived from microbial fermentation using a gas containing carbon monoxide and hydrogen as a substrate has a retention time with a peak of 5 minutes 30 seconds to 5 minutes 35 seconds in addition to a peak of 2 minutes 55 seconds to 3 minutes 5 seconds. For the same reason as described above, it is considered that even ethanol obtained through a purification process such as distillation contains a substance having a boiling point very close to that of ethanol such as an aldehyde compound, and it is considered that the plurality of unavoidable substances exert some action in a reaction step using ethanol as a raw material to improve the ethanol conversion rate and the reaction rate.

The ethanol of the present invention is obtained by extracting and further purifying an ethanol-containing liquid obtained from a microbial fermentation tank as described later, but the ethanol may contain other components described below in addition to the above-mentioned unavoidable substances. For example, a trace amount of an aromatic compound may be contained. Examples of the aromatic compound contained in ethanol include toluene, ethylbenzene, o-xylene, m-xylene, and p-xylene. Only one of these aromatic compounds may be contained, or two or more aromatic compounds may be contained. As the aromatic compound, ethylbenzene is preferably contained.

The lower limit of the content (sum) of aromatic compound contained in ethanol is 0.001 mg/L or more, preferably 0.01 mg/L or more, more preferably 0.1 mg/L or more, further preferably 0.4 mg/L or more, and particularly preferably 1.0 mg/L or more with respect to the entire ethanol. The upper limit of the content (sum) of the aromatic compound contained in ethanol is 100 mg/L or less, preferably 50 mg/L or more, more preferably 1 mg/L or less, further more preferably 7 mg/L or less, and particularly preferably 3.0 mg/L or less.

When the aromatic compound content is within the above-mentioned numerical range, it is possible to improve the ethanol conversion rate when butadiene is synthesized using ethanol as a raw material, to improve the reaction rate when carboxylic acid ester is synthesized by adding ethanol to carboxylic acid, or to improve the combustion efficiency when ethanol is used as a fuel.

In the case where the aromatic compound is ethylbenzene, the content of ethylbenzene is preferably 0.1 mg/L or more, more preferably 0.2 mg/L or more, further preferably 0.3 mg/L or more, further more preferably 0.5 mg/L or more, and preferably 5 mg/L or less, more preferably 3 mg/L or less, further preferably 2 mg/L or less, and further more preferably 1 mg/L or less with respect to the entire ethanol. When the content of ethylbenzene is within the above numerical value range, it is possible to improve the ethanol conversion rate when butadiene is synthesized using ethanol as a raw material, to improve the reaction rate when carboxylic acid ester is synthesized by adding ethanol to carboxylic acid, or to improve the combustion efficiency when ethanol is used as a fuel.

When the aromatic compound is toluene, the content of toluene is preferably 0.01 mg/L or more, more preferably 0.02 mg/L or more, further preferably 0.03 mg/L or more, further more preferably 0.05 mg/L or more, and preferably 1 mg/L or less, more preferably 0.5 mg/L or less, further preferably 0.2 mg/L or less, and further more preferably 0.1 mg/L or less with respect to the entire ethanol. When the content of toluene is within the above numerical value range, it is possible to improve the ethanol conversion rate when butadiene is synthesized using ethanol as a raw material, to improve the reaction rate when carboxylic acid ester is synthesized by adding ethanol to carboxylic acid, or to improve the combustion efficiency when ethanol is used as a fuel.

When the aromatic compound is o-xylene, the content of o-xylene is preferably 0.1 mg/L or more, more preferably 0.2 mg/L or more, further preferably 0.3 mg/L or more, further more preferably 0.5 mg/L or more, and preferably 5 mg/L or less, more preferably 3 mg/L or less, further preferably 2 mg/L or less, and further more preferably 1 mg/L or less, with respect to the entire ethanol. When the content of o-xylene is within the above numerical value range, it is possible to improve the ethanol conversion rate when butadiene is synthesized using ethanol as a raw material, to improve the reaction rate when carboxylic acid ester is synthesized by adding ethanol to carboxylic acid, or to improve the combustion efficiency when ethanol is used as a fuel.

When the aromatic compound is m-xylene and/or p-xylene, the content (sum) of m-xylene and/or p-xylene is preferably 0.2 mg/L or more, more preferably 0.3 mg/L or more, further preferably 0.4 mg/L or more, further more preferably 0.5 mg/L or more, and preferably 5 mg/L or less, more preferably 3 mg/L or less, further preferably 2 mg/L or less, and further more preferably 1 mg/L or less with respect to the total ethanol. When the content of m-xylene and/or p-xylene is within the above-mentioned numerical range, it is possible to improve the ethanol conversion rate when butadiene is synthesized from ethanol as a raw material, to improve the reaction rate when carboxylic acid is synthesized by adding ethanol to carboxylic acid, or to improve the combustion efficiency when ethanol is used as a fuel.

The ethanol according to the present invention may further contain a small amount of aliphatic hydrocarbons. Examples of the aliphatic hydrocarbons include n-hexane, n-heptane, n-octane, n-dodecane, and n-tetradecane. Only one of these aliphatic hydrocarbons may be contained, or two or more aliphatic hydrocarbons may be contained. As the aromatic compound, one or more of n-hexane and n-dodecane are preferably contained.

The content (total amount) of aliphatic hydrocarbon contained in ethanol is preferably 0.001 mass ppm or more, preferably 0.005 mass ppm or more, more preferably 0.01 mass ppm or more, further preferably 0.1 mass ppm or more, and 100 mass ppm or less, preferably 50 mass ppm or less, more preferably 10 mass ppm or less, and further more preferably 5 mass ppm or less with respect to the entire ethanol.

In the case where n-hexane is contained in ethanol, the content of n-hexane is preferably 0.1 mass ppm or more, more preferably 0.2 mass ppm or more, further preferably 0.3 mass ppm or more, further more preferably 0.5 mass ppm or more, and preferably 5 mass ppm or less, more preferably 3 mass ppm or less, further preferably 2 mass ppm or less, further more preferably 1 mass ppm or less, with respect to the entire ethanol.

When n-heptane is contained in ethanol, the content of n-heptane is preferably 0.01 mass ppm or more, more preferably 0.02 mass ppm or more, further preferably 0.03 mass ppm or more, further more preferably 0.05 mass ppm or more, and preferably 1 mass ppm or less, more preferably 0.5 mass ppm or less, further preferably 0.2 mass ppm or less, and further more preferably 0.1 mass ppm or less, with respect to the entire ethanol.

In the case where n-octane is contained in ethanol, the content of n-octane is preferably 0.01 mass ppm or more, more preferably 0.02 mass ppm or more, further preferably 0.03 mass ppm or more, further more preferably 0.05 mass ppm or more, and preferably 1 mass ppm or less, more preferably 0.5 mass ppm or less, further preferably 0.2 mass ppm or less, and further more preferably 0.1 mass ppm or less with respect to the entire ethanol.

In the case where n-dodecane is contained in ethanol, the content of n-dodecane is preferably 0.01 mass ppm or more, more preferably 0.02 mass ppm or more, further preferably 0.03 mass ppm or more, further more preferably 0.05 mass ppm or more, and preferably 1 mass ppm or less, more preferably 0.5 mass ppm or less, further preferably 0.2 mass ppm or less, and further more preferably 0.1 mass ppm or less with respect to the entire ethanol.

In the case where n-tetradecane is contained in ethanol, the content of n-tetradecane is preferably 0.01 mass ppm or more, more preferably 0.02 mass ppm or more, further preferably 0.03 mass ppm or more, further more preferably 0.05 mass ppm or more, and preferably 1 mass ppm or less, more preferably 0.5 mass ppm or less, further preferably 0.2 mass ppm or less, and further more preferably 0.1 mass ppm or less with respect to the entire ethanol.

The ethanol according to the present invention may further contain a trace amount of a dialkyl ether. Examples of the dialkyl ether include dimethyl ether, diethyl ether, dipropyl ether, dibutyl ether, and dipentyl ether. Only one two or more of these may be contained. As the dialkyl ether, dibutyl ether is preferably contained.

The content (sum) of dialkyl ether contained in ethanol is preferably 0.001 mg/L or more, preferably 0.01 mg/L or more, more preferably 0.1 mg/L or more, further preferably 1.0 mg/L or more, and 100 mg/L or less, preferably 80 mg/L or less, more preferably 50 mg/L or less, and further preferably 30 mg/L or less with respect to the entire ethanol. When the content of the dialkyl ether is within the above-mentioned numerical range, it is possible to improve the ethanol conversion rate when butadiene is synthesized using ethanol as a raw material, to improve the reaction rate when carboxylic acid ester is synthesized by adding ethanol to carboxylic acid, or to improve the combustion efficiency when ethanol is used as a fuel.

When dibutyl ether is contained in ethanol, the content of dibutyl ether is preferably 1 mg/L or more, more preferably 2 mg/L or more, further preferably 5 mg/L or more, further more preferably 10 mg/L or more, and preferably 50 mg/L or less, more preferably 40 mg/L or less, further preferably 30 mg/L or less, and further more preferably 25 mg/L or less with respect to ethanol. When the content of dibutyl ether is within the above-mentioned numerical range, it is possible to improve the ethanol conversion rate when butadiene is synthesized using ethanol as a raw material, to improve the reaction rate when carboxylic acid ester is synthesized by adding ethanol to carboxylic acid, or to improve the combustion efficiency when ethanol is used as a fuel.

The ethanol of the present invention contains an extremely small amount of the above-mentioned organic compound, but it may also contain a compound containing an element such as Si, K, Na, Fe, Cr, etc. The compound containing these elements may be an inorganic compound or an organometallic compound. For example, in the case of containing Si, silica or organosiloxane may be contained.

When Si is contained in ethanol, the content of Si with respect to ethanol is preferably 10 mg/L or more, more preferably 20 mg/L or more, further preferably 30 mg/L or more, and preferably 100 mg/L or less, more preferably 90 mg/L or less, and further preferably 80 mg/L or less. The content of Si is an amount equivalent to Si element in the Si compound. When the content of Si is within the above-mentioned numerical range, it is possible to improve the ethanol conversion rate when butadiene is synthesized using ethanol as a raw material, to improve the reaction rate when carboxylic acid ester is synthesized by adding ethanol to carboxylic acid, or to improve the combustion efficiency when ethanol is used as a fuel.

When K is contained in ethanol, the content of K with respect to ethanol is preferably 1.0 mg/L or more, more preferably 1.5 mg/L or more, further preferably 2.0 mg/L or more, further more preferably 2.5 mg/L or more, and preferably 10 mg/L or less, more preferably 7 mg/L or less, and further preferably 5 mg/L or less. The content of K is an amount equivalent to the K element of the K compound. When the content of K is within the above-mentioned numerical range, it is possible to improve the ethanol conversion rate when butadiene is synthesized using ethanol as a raw material, to improve the reaction rate when carboxylic acid is synthesized by adding ethanol to carboxylic acid, or to improve the combustion efficiency when ethanol is used as a fuel.

When Na is contained in ethanol, the content of Na with respect to ethanol is preferably 150 mg/L or more, more preferably 170 mg/L or more, further preferably 190 mg/L or more, and preferably 1000 mg/L or less, more preferably 500 mg/L or less, further preferably 400 mg/L or less, and further more preferably 300 mg/L or less. The content of Na is an amount equivalent to the Na element of the Na compound. When the content of Na is within the above-mentioned numerical range, it is possible to improve the ethanol conversion rate when butadiene is synthesized using ethanol as a raw material, to improve the reaction rate when carboxylic acid is synthesized by adding ethanol to carboxylic acid, or to improve the combustion efficiency when ethanol is used as a fuel.

When Fe is contained in ethanol, the content of Fe with respect to ethanol is preferably 2.0 mg/L or less, more preferably 1.5 mg/L or less, further preferably 1.0 mg/L or less, and further more preferably 0.5 mg/L or less. The content of Fe is an amount equivalent to the Fe element of the Fe compound. When the content of Fe is within the above-range, it is possible to improve the ethanol conversion rate when butadiene is synthesized using ethanol as a raw material, to improve the reaction rate when a carboxylic acid ester is synthesized by adding ethanol to a carboxylic acid, or to improve the combustion efficiency when ethanol is used as a fuel.

When Cr is contained in ethanol, the content of Cr is preferably 0.6 mg/L or less, and more preferably 0.5 mg/L or less with respect to ethanol. The content of Cr is an amount equivalent to the Cr element of the Cr compound. When the content of Cr is within the above-mentioned numerical range, it is possible to improve the ethanol conversion rate when butadiene is synthesized using ethanol as a raw material, to improve the reaction rate when carboxylic acid ester is synthesized by adding ethanol to carboxylic acid, or to improve the combustion efficiency when ethanol is used as a fuel.

The ethanol of the present invention contains an inorganic component as described above and, if desired, a small amount of an organic component such as an aromatic hydrocarbon or an aliphatic hydrocarbon, but the concentration of ethanol (pure ethanol as a compound), which is the main component in ethanol, is 75% by volume or more, preferably 80% by volume or more, more preferably 90% by volume or more, further preferably 95% by volume or more, further more preferably 98% by volume or more, and preferably 99.999% by volume or less, more preferably 990.99% by volume or less, further preferably 99.9% by volume or less, and further more preferably 99.5% by volume or less, with respect to the entire ethanol.

The ethanol concentration in the ethanol of the present invention may be set according to the intended purpose, for example, in the case of cosmetics or the like, those with 90% by volume or more is preferably used, in the case of ethanol for disinfectants, those with 75% by volume or more is preferably used, and the upper limit can also be conveniently set according to the purpose. From the viewpoint of transportation cost and the like, the higher the concentration of ethanol is, the more preferable as a product.

<Method for Manufacturing Ethanol>

As a method for manufacturing ethanol having a specific gas chromatographic peak as described above, for example, ethanol can be produced by microbial fermentation of a synthetic gas containing carbon monoxide derived from waste or exhaust gas. In such a process, the content of aromatic compounds and the like in the raw material gas derived from waste or exhaust gas and the purification conditions may be controlled so as to control the amount of aromatic compounds contained in the final product. Hereinafter, as an example, a method for manufacturing ethanol from a synthetic gas containing carbon monoxide derived from waste or exhaust gas by microbial fermentation will be described.

A method for producing ethanol comprises the step of converting a carbon source into a synthetic gas comprising carbon monoxide and hydrogen;
a microbial fermentation step of supplying the synthetic gas comprising carbon monoxide and hydrogen to a microbial fermentation tank to obtain an ethanol-containing liquid by microbial fermentation; a separation step of separating the ethanol-containing liquid into a liquid or solid component containing microorganisms and a gas component containing ethanol; a liquefaction step of condensing and liquefying the gas component; a purification step of purifying ethanol from the liquid obtained in the liquefaction step; but may optionally comprise a raw material gas generation step, a synthetic gas preparation step, a wastewater treatment step, and the like. Each step will be described below.

<Raw Material Gas Generation Step>

The raw material gas generation step is a step of generating a raw material gas by gasifying a carbon source in the gasification unit. In the raw material gas generation step, a gasification furnace may be used. The gasification furnace is a furnace for burning (incomplete combustion) a carbon source, and examples thereof include a shaft furnace, a kiln furnace, a fluidized bed furnace, and a gasification reforming furnace. The gasification furnace is preferably a fluidized bed furnace type since high hearth load and excellent operability can be achieved by partial combustion of waste. The waste is gasified in a fluidized bed furnace of low temperature (about 450 to 600° C.) and low oxygen atmosphere to decompose into gas (carbon monoxide, carbon dioxide, hydrogen, methane, etc.) and carbon-rich char. Furthermore, the incombustibles contained in the waste are separated from the bottom of the furnace in a hygienic and low oxidation state, so that valuable materials such as iron and aluminum contained in the incombustibles can be selectively recovered. Therefore, the gasification of waste enables efficient resource recycling.

The temperature of the gasification in the raw material gas generation step is, without particular limitation, usually 100 to 2500° C. and preferably 200 to 2100° C.

The reaction time of gasification in the raw material gas generation step is usually 2 seconds or more, preferably 5 seconds or more.

The carbon source used in the raw material gas generation step is not particularly limited, and various carbon-containing materials such as coal used in a coke oven of a steel plant, a blast furnace (blast furnace gas), a converter or a coal-fired power plant, general waste and industrial waste introduced into an incinerator (especially a gasification furnace), carbon dioxide produced as a by-product by various industries, and the like can also be suitably used for the purpose of recycling.

More specifically, the carbon source is preferably waste, specifically, plastic waste, raw garbage, municipal solid waste (MSW), industrial solid waste, waste tires, biomass waste, household waste such as duvet and paper, waste such as building members, coal, petroleum, petroleum-derived compounds, natural gas, shale gas, and the like, among which various types of waste are preferable, and from the viewpoint of separation cost, unseparated municipal solid waste is more preferable.

The raw material gas obtained by gasifying the carbon source contains carbon monoxide and hydrogen as essential components, but may further contain carbon dioxide, oxygen and nitrogen. As other components, the raw material gas may further contain components such as soot, tar, a nitrogen compound, a sulfur compound, a phosphorus compound, an aromatic compound and the like.

The raw material gas may be produced as a gas containing, without particular limitation, 0.1% by volume or more, preferably 10% by volume or more, more preferably 20% by volume or more of carbon monoxide by performing heat treatment (commonly known as gasification) for burning a carbon source (incomplete combustion) in the raw material gas production process, that is, by partially oxidizing the carbon source.

<Synthetic Gas Purification Step>

The synthetic gas purification step is a step of removing or reducing specific substances such as various contaminants, soot and dust particles, impurities, and undesirable amounts of compounds from the raw material gas. When the raw material gas is derived from waste, the raw material gas usually contains 0.1% by volume or more and 80% by volume or less of carbon monoxide, 0.1% by volume or more and 70% by volume or less of carbon dioxide, 0.1% by volume or more and 80% by volume or less of hydrogen, and tends to contain 1 mg/L or more of a nitrogen compound, 1 mg/L or more of a sulfur compound, 0.1 mg/L or more of a phosphorus compound, and/or 10 mg/L or more of an aromatic compound. It may also contain other substances such as other environmental pollutants, soot and dust particles and impurities. Therefore, when the synthetic gas is supplied to the microbial fermentation tank, it is preferable to reduce or remove from the raw material gas substances that are not preferable for stable cultivation of microorganisms or an undesirable amount of a compound so that the content of each component contained in the raw material gas is within a range suitable for stable cultivation of microorganisms.

Particularly in the synthetic gas purification step, carbon dioxide gas in the synthetic gas is adsorbed on the regeneration adsorbent (zeolite) by using a pressure swing adsorption device filled with the regeneration adsorbent, thereby reducing the concentration of carbon dioxide gas in the synthetic gas. Further, the synthetic gas may be subjected to other treatment steps known in the art to remove the impurities and adjust the gas composition. Other treatment steps include, for example, treatment using one or two or more of a gas chiller (water separator), a low-temperature separation system (deep cooling system) separator, a fine particle (soot) separator such as a cyclone or bag filter, a scrubber (water-soluble impurity separator), a desulfurization device (sulfide separator), a membrane separation system separator, a deoxygenator, a pressure swing adsorption system separator (PSA), a temperature swing adsorption system separator (TSA), a pressure temperature swing adsorption system separator (PTSA), a separation system using activated carbon, a deoxygenator catalyst, specifically a separation system using a copper catalyst or a palladium catalyst, or the like.

The synthetic gas used in the ethanol manufacturing method of the present invention contains at least carbon monoxide as an essential component, and may further contain hydrogen, carbon dioxide and nitrogen.

As for the synthetic gas used in the present invention, it is possible to use as the synthetic gas a gas obtained by generating a raw material gas by gasifying a carbon source (raw material gas generation step), and then performing a step of reducing or removing substances and compounds as described above together with adjusting the concentration of each component of carbon monoxide, carbon dioxide, hydrogen and nitrogen from the raw material gas.

The carbon monoxide concentration in the synthetic gas is usually 20% by volume to 80% by volume, preferably 25% by volume to 50% by volume, more preferably 35% by volume to 45% by volume, with respect to the total concentration of carbon monoxide, carbon dioxide, hydrogen and nitrogen in the synthetic gas.

The hydrogen concentration in the synthetic gas is usually 10% by volume to 80% by volume, preferably 30% by volume to 55% by volume, more preferably 40% by volume to 50% by volume, with respect to the total concentration of carbon monoxide, carbon dioxide, hydrogen and nitrogen in the synthetic gas.

The carbon dioxide concentration in the synthetic gas is usually 0.1% by volume to 40% by volume, preferably 0.3% by volume to 30% by volume, more preferably 0.5% by volume to 10% by volume, and particularly preferably 1% by volume to 6% by volume with respect to the total concentration of carbon monoxide, carbon dioxide, hydrogen and nitrogen in the synthetic gas.

The nitrogen concentration in the synthetic gas is usually 40% by volume or less, preferably 1% by volume to 20% by volume, more preferably 5% by volume to 15% by volume, with respect to the total concentration of carbon monoxide, carbon dioxide, hydrogen, and nitrogen in the synthetic gas.

The concentrations of carbon monoxide, carbon dioxide, hydrogen and nitrogen can be set within a predetermined range by changing the elemental composition of hydrocarbon (carbon and hydrogen) of the carbon source and nitrogen in the raw material gas generation step, or by appropriately changing the combustion conditions such as the combustion temperature and the oxygen concentration of the supply gas during combustion. For example, in the case where one wish to change the concentration of carbon monoxide or hydrogen, there is a method in which the ratio of hydrocarbons (carbon and hydrogen) such as waste plastics is changed to a carbon source having a high ratio, and in the case where one wish to reduce the concentration of nitrogen, a gas having a high oxygen concentration is supplied in the raw material gas generation step.

The synthetic gas used in the present invention is not particularly limited in addition to the components described above, and may contain a sulfur compound, a phosphorus compound, a nitrogen compound, and the like. The content of each of these compounds is preferably 0.05 mg/L or more, more preferably 0.1 mg/L or more, further preferably 0.5 mg/L or more, and preferably 2000 mg/L or less, more preferably 1000 mg/L or less, further preferably 80 mg/L or less, further more preferably 60 mg/L or less, and particularly preferably 40 mg/L or less. When the contents of the sulfur compound, the phosphorus compound, the nitrogen compound and the like is not less than the lower limit value, there is an advantage that the microorganisms can be cultured suitably, and when the contents are not more than the upper limit value, there is an advantage that the medium is not contaminated by various nutrients not consumed by the microorganisms.

Sulfur compounds usually include sulfur dioxide, $CS_2$, COS, and $H_2S$, among which $H_2S$ and sulfur dioxide are preferred because they are easily consumed as a source of nutrients for microorganisms. Therefore, it is more preferable that the synthetic gas contains the sum of $H_2S$ and sulfur dioxide within the above range. As the phosphorus compound, it is preferable that phosphoric acid is easily consumed as a nutrient source for microorganisms. For this reason, it is more preferable that phosphoric acid is contained in the synthetic gas within the above range.

Examples of the nitrogen compound include nitrogen monoxide, nitrogen dioxide, acrylonitrile, acetonitrile, HCN, and the like, and HCN is preferable because it is easy to consume as a nutrient source for microorganisms. Therefore, it is more preferable that HCN is contained in the synthetic gas within the above range.

The synthetic gas may contain an aromatic compound of 0.01 mg/L or more and 90 mg/L or less, preferably 0.03 mg/L or more, more preferably 0.05 mg/L or more, further preferably 0.1 mg/L or more, and preferably 70 mg/L or less, more preferably 50 mg/L or less, further preferably 30 mg/L or less. When the content is not lower than the lower limit value, microorganisms tend to be cultured suitably, and when the content is not higher than the upper limit value, the medium tends to be less contaminated by various nutritional sources not consumed by microorganisms.

<Microbial Fermentation Step>

The microbial fermentation step is a method for manufacturing ethanol by subjecting the synthetic gas described above to microbial fermentation in a microbial fermentation tank. Preferably, the microbial fermentation tank is a continuous fermentation apparatus. In general, the microbial fermentation tank can be of any shape, including a stirring type, an air lift type, a bubble column type, a loop type, an open bond type, and a photo-bio type, but in the present invention, suitable use is made to a known loop reactor in which the microbial fermentation tank has a main tank portion and a reflux portion. In this case, it is preferable to further comprise a circulation step in which the liquid medium is circulated between the main tank portion and the reflux portion.

As the synthetic gas to be supplied to the microbial fermentation tank, the gas obtained through the raw material gas generation step may be used as the synthetic gas as it is, as long as the component conditions of the synthetic gas described above are satisfied, or the synthetic gas may be used after adding another predetermined gas to the gas obtained by reducing or removing impurities from the raw material gas. As another predetermined gas, for example, at least one compound selected from the group consisting of a sulfur compound such as sulfur dioxide, a phosphorus compound, and a nitrogen compound may be added to form a synthetic gas.

Although the synthetic gas and the microbial culture solution may be continuously supplied to the microbial fermentation tank, it is not necessary to supply the synthetic gas and the microbial culture solution at the same time, but the synthetic gas may be supplied to the microbial fermentation tank to which the microbial culture solution has been supplied in advance. It is known that certain anaerobic microorganisms produce ethanol or the like from a substrate gas such as synthetic gas by fermenting action, and such gas-utilizing microorganisms are cultured in a liquid medium. For example, a liquid medium and the gas-utilizing bacteria may be supplied and contained, and the synthetic gas may be supplied into the microbial fermentation tank while the liquid medium is stirred in this state. Thus, the gas-utilizing bacteria may be cultured in the liquid medium, and ethanol can be produced from the synthetic gas by the fermentation action thereof.

In the microbial fermentation tank, any temperature may be employed for the temperature of the medium or the like (culture temperature), preferably about 30 to 45° C., more preferably about 33 to 42° C., and further preferably about 36.5 to 37.5° C. The culture time is preferably 12 hours or more, more preferably 7 days or more, particularly preferably 30 days or more, and most preferably 60 days or more in continuous culture, and although there is no particular limitation, the upper limit is preferably 720 days or less, and more preferably 365 days or less from the viewpoint of regular maintenance of the facility or the like. The culture time is to be noted that it means the time from the addition of the seed bacteria to the culture tank to the discharge of the entire culture medium in the culture tank.

The microorganisms (species) contained in the microorganism culture solution are not particularly limited as long as ethanol can be produced by microbial fermentation of synthetic gas using carbon monoxide as the main raw material. For example, it is preferable that the microorganisms (species) produce ethanol from synthetic gas by the fermentation action of gas-utilizing bacteria, and in particular, that the microorganisms have a metabolic pathway of acetyl COA. Among the gas-utilizing bacteria, the genus *Clostridium* is more preferable, and *Clostridium autoethanogenum* is particularly preferable, without limitation. Examples will be further described below.

Gas-utilizing bacteria include both eubacteria and archaebacteria. Examples of eubacteria include *Clostridium* spp., *Moorella* spp., *Acetobacterium* spp., *Carboxydocella* spp., *Rhodopseudomonas* spp., *Eubacterium* spp., *Butyribacterium* spp., *Oligotropha* spp., *Bradyrhizobium* spp., and *Ralsotonia* spp., which is an aerobic hydrogen-oxidizing bacteria.

On the other hand, examples of the archaebacterium include *Methanobacterium* spp., *Methanobrevibacter* spp., *Methanocalculus* spp., *Methanococcus* spp., *Methanosarcina* spp., *Methanosphaera* spp., *Methanothermobacter* spp., *Methanothrix* spp., *Methanoculleus* spp., *Methanofollis* spp., *Methanogenium* spp., *Methanospirillium* spp., *Methanosaeta* spp., *Thermococcus* spp., *Thermofilum* spp., and *Arcaheoglobus* spp. Among these, *Methanosarcina* spp., *Methanococcus* spp., *Methanothermobacter* spp., *Methanothrix* spp., *Thermococcus* spp., *Thermofilum* spp., and *Archaeoglobus* spp. are preferable as archaebacteria.

Further, since the utilization of carbon monoxide and carbon dioxide is excellent, *Methanosarcina* spp., *Methanothermobactor* spp., or *Methanococcus* spp. are preferable as the archaebacterium, and *Methanosarcina* spp., or *Methanococcus* spp. are particularly preferable as the archaebacterium. Specific examples of the *Methanosarcina* spp. include *Methanosarcina barkeri*, *Methanosarcina mazei*, and *Methanosarcina acetivorans*.

From the above-mentioned gas-assimilable bacteria, a bacterium having a high ability to produce the desired ethanol is selected and used. Examples of the gas-assimilable bacteria having a high ability to produce ethanol include *Clostridium autoethanogenum*, *Clostridium ljungdahlii*, *Clostridium aceticum*, *Clostridium carboxydivorans*,

*Moorella thermoacetica, Acetobacterium woodii*, and the like. Among these, *Clostridium autoethanogenum* is particularly preferred.

The medium used for culturing the above-mentioned microorganisms (species) is not particularly limited as long as it has an appropriate composition according to the bacteria, but is a liquid containing water as the main component and nutrients (e.g., vitamins, phosphoric acid, etc.) dissolved or dispersed in the water. The composition of such medium is adjusted so that gas-utilizing bacteria can grow well. For example, a medium for the use of *Clostridium* as a microorganism can be obtained by referring to paragraphs [0097] to [0099] in U.S. Patent Application Publication No. 2017/260552.

The ethanol-containing liquid obtained by the microbial fermentation step can be obtained as a suspension containing microorganisms, dead microorganisms, proteins derived from microorganisms, and the like. The protein concentration in the suspension is usually between 30 and 1000 mg/L, depending on the type of microorganism. The protein concentration in the ethanol-containing solution can be measured by the Kjeldahl method.

<Separation Step>

The ethanol-containing liquid obtained in the microbial fermentation step is then subjected to a separation step. In the present invention, the ethanol-containing liquid is heated to room temperature to 500° C. under conditions of 0.01 to 1000 kPa (absolute pressure) to separate the liquid or solid component containing microorganisms and the gas component containing ethanol. In the conventional method, the ethanol-containing liquid obtained by the microbial fermentation step is distilled to separate and purify the desired ethanol; however, since the ethanol-containing liquid contains microorganisms, proteins derived from microorganisms, and the like, foaming occurred in the distillation apparatus when the ethanol-containing liquid was distilled as it is, sometimes inhibiting continuous operation. Although it is known to use a membrane evaporator as a method for purifying a foaming liquid, the membrane evaporator has low concentration efficiency and is not suitable for purification of a liquid containing a solid component. In the present invention, the ethanol-containing liquid is heated and separated into a liquid or a solid component containing microorganisms and a gas component containing ethanol, before separating and purifying the desired ethanol from an ethanol-containing liquid obtained by a microbial fermentation step by a distillation operation or the like, and the desired ethanol is separated and purified only from the separated gas component containing ethanol. The distillation operation can be carried out continuously by carrying out the separation step because foaming does not occur in the distillation apparatus in the distillation operation at the time of separating and purifying ethanol. Further, since the concentration of ethanol contained in the gas component containing ethanol is higher than the ethanol concentration in the ethanol-containing liquid, ethanol can be efficiently separated and purified in the purification step to be described later.

In the present invention, the ethanol-containing liquid is heated under conditions of preferably 10 to 200 kPa, more preferably 50 to 150 kPa, further preferably under atmospheric pressure, preferably at a temperature of 50 to 200° C., more preferably at a temperature of 80 to 180° C., and further preferably at a temperature of 100 to 150° C., from the viewpoint of efficient separation into liquid or solid components containing microorganisms, dead microorganisms, proteins derived from microorganisms, and the like, and gas components containing ethanol.

The heating time in the separation step is not particularly limited as long as the gas component can be obtained, but from the viewpoint of efficiency or economy, it is usually 5 seconds to 2 hours, preferably 5 seconds to 1 hour, and more preferably 5 seconds to 30 minutes.

The separation step described above can be used without particular limitation as long as it is an apparatus capable of efficiently separating an ethanol-containing liquid into a liquid or a solid component (microorganisms, dead microorganisms, proteins derived from microorganisms, or the like) and a gas component (ethanol) by thermal energy, and drying apparatuses such as a rotary dryer, a fluidized bed dryer, a vacuum type dryer, and a conduction heating type dryer can be used, but it is preferable to use a conduction heating type dryer from the viewpoint of efficiency when separating the liquid or solid component and the gas component from an ethanol-containing liquid having a particularly low solid component concentration. Examples of the conduction heating type dryer include a drum type dryer, a disk type dryer and the like.

<Liquefaction Step>

The liquefaction step is a step of liquefying the gas component containing ethanol obtained in the separation step by condensation. The apparatus used in the liquefaction step is not particularly limited, but it is preferable to use a heat exchanger, particularly a condenser. Examples of the condenser include a water-cooled condenser, an air-cooled condenser, and an evaporative condenser. Among these, a water-cooled condenser is preferable. The condenser may have a single stage or a plurality of stages.

It can be said that it is preferable that the liquefied product obtained by the liquefaction process does not contain components contained in the ethanol-containing liquid, such as microorganisms, dead microorganisms, or proteins derived from microorganisms, but the present invention does not exclude the fact that proteins are contained in the liquefied product. Even when proteins are contained in the liquefied product, the concentration thereof is preferably 40 mg/L or less, more preferably 20 mg/L or less, further preferably 15 mg/L or less.

The condensation heat of the gas component obtained by the condenser may be reused as a heat source in the purification step described later. By reusing the condensation heat, ethanol can be produced efficiently and economically.

<Purification Step>

Next, ethanol is purified from the liquefied product obtained in the liquefaction step. The ethanol-containing liquid obtained in the microbial fermentation step can be supplied to the purification step without going through the separation step described above when components such as microorganisms have already been removed. The purification step is a step in which the ethanol-containing liquid obtained in the liquefaction step is separated into a distillate having a higher concentration of the target ethanol and a bottoms product having a lower concentration of the target ethanol. Examples of the apparatus used in the purification step include a distillation apparatus, a treatment apparatus including a pervaporation membrane, a treatment apparatus including a zeolite dehydration membrane, a treatment apparatus for removing a low boiling point substance having a boiling point lower than that of ethanol, a treatment apparatus for removing a high boiling point substance having a boiling point higher than that of ethanol, a treatment apparatus including an ion exchange membrane, and the like.

These apparatuses may be used alone or in combination of two or more types. As the unit operation, heating distillation or membrane separation may be suitably used.

In heating distillation, the desired ethanol can be obtained in high purity as a distillate using a distillation apparatus. The temperature in the distillation still at the time of distillation of ethanol is not particularly limited, but is preferably 100° C. or lower, more preferably about 70 to 95° C. By setting the temperature in the distillation still within the above range, separation of ethanol from other components, that is, distillation of ethanol can be performed even more surely.

In particular, high-purity ethanol can be obtained by introducing an ethanol-containing liquid obtained in the liquefaction step into a distillation apparatus equipped with a heater using steam at 100° C. or higher, raising the temperature of the bottom of the distillation column to 90° C. or higher within 30 minutes, introducing the ethanol-containing liquid from the middle of the distillation column, and performing the distillation step with the temperature difference between the parts of the bottom, middle, and top of the column within ±15° C. The distillation temperature difference is preferably ±13° C., more preferably ±11° C. With the difference in distillation temperature, separation from other components, that is, distillation of ethanol can be performed even more surely.

The ethanol-containing liquid is considered to contain tetradecane or decane, having a boiling point higher than that of ethanol. In the present invention, by adjusting the above-mentioned distillation conditions, for example, by raising the temperature at the top of the distillation column to 5 to 10° C. higher than usual, the aromatic compound is also distilled, whereby the aromatic compound contained in the ethanol contained in the distillate can be adjusted. As a result, the content of the aromatic compound in the final ethanol can be adjusted.

When ethanol is distilled, the pressure in the distillation apparatus may be normal pressure, preferably less than atmospheric pressure, and more preferably about 60 to 95 kPa (absolute pressure). By setting the pressure in the distillation apparatus within the above range, the separation efficiency of ethanol can be improved, and thus the yield of ethanol can be improved. The yield of ethanol (the concentration of ethanol contained in the distillate after distillation) is preferably 90% by volume or more, more preferably 95% by volume or more.

A known separation membrane can be appropriately used in the membrane separation, and for example, a zeolite membrane can be suitably used.

The concentration of ethanol contained in the distillate separated in the purification step is preferably 20 volume % to 99.99 volume %, more preferably 60 volume % to 99.9 volume %.

On the other hand, the concentration of ethanol contained in the bottoms product is preferably 0.001 volume % to 10 volume %, more preferably 0.01 volume % to 5 volume %.

The bottoms product separated in the purification step is substantially free of nitrogen compounds. In the present invention, "substantially free" does not mean that the concentration of nitrogen compounds is 0 mg/L, but means that the bottoms product obtained in the purification step has a nitrogen compound concentration of a level that does not require a wastewater treatment step. In the separation step, the desired ethanol is not purified from the ethanol-containing liquid obtained in the microbial fermentation step, but the ethanol-containing liquid is separated into a liquid or a solid component containing microorganisms and a gas component containing ethanol as described above. In this process, the nitrogen compound remains on the liquid or solid component side containing microorganisms, so that the gas component containing ethanol contains almost no nitrogen compound. Therefore, it is considered that the bottoms product obtained at the time of purifying ethanol from the liquefied product obtained by liquefying the gas component contains substantially no nitrogen compound. Even when the bottoms product is contained in the nitrogen compound, the concentration of the nitrogen compound is 0.1 to 200 mg/L, preferably 0.1 to 100 mg/L, more preferably 0.1 to 50 mg/L.

For the same reason as described above, the bottoms product separated in the purification step does not substantially contain phosphorus compounds. The term "substantially free" does not mean that the concentration of phosphorus compounds is 0 mg/L, but means that the bottoms product obtained in the purification step has a phosphorus compound concentration of a level that does not require a wastewater treatment step. Even when the bottoms product is contained in the phosphorus compound, the concentration of phosphorus compound is 0.1 to 100 mg/L, preferably 0.1 to 50 mg/L, more preferably 0.1 to 25 mg/L. Thus, according to the method of the present invention, it is considered that the bottoms product discharged in the ethanol purification step substantially contains no nitrogen compound or phosphorus compound and hardly contains any other organic substances, and thus it is possible to simplify the wastewater treatment step conventionally required.

<Wastewater Treatment Step>

The bottoms product separated in the purification step may be supplied to the wastewater treatment step. In the wastewater treatment step, organic substances such as nitrogen compounds and phosphorus compounds can be further removed from the bottoms product. In this process, organic substances can be removed by subjecting the bottoms product to anaerobic treatment or aerobic treatment. The removed organic substances can be used as a fuel (heat source) in the purification step.

The treatment temperature in the waste water treatment step is usually 0 to 90° C., preferably 20 to 40° C., more preferably 30 to 40° C.

Since liquid or solid components containing microorganisms and the like are removed from the bottoms product obtained through the separation step, the load of waste water treatment and the like is reduced compared with the bottoms product obtained by being supplied directly from the microbial fermentation step to the purification step.

In the waste water treatment step, the concentration of the nitrogen compound in the treatment liquid obtained by treating the bottoms product is preferably 0.1 to 30 mg/L, more preferably 0.1 to 20 mg/L, further preferably 0.1 to 10 mg/L, and it is particularly preferable that the nitrogen compound is not contained. In the waste water treatment step, the concentration of the phosphorus compound in the treatment liquid is preferably 0.1 to 10 mg/L, more preferably 0.1 to 5 mg/L, further preferably 0.1 to 1 mg/L, and it is particularly preferable that the phosphorus compound is not contained.

<Use of Ethanol>

Ethanol according to the present invention can be used as a raw material for manufacturing various organic compounds. For example, ethanol according to the present invention can be used as a raw material for manufacturing butadiene, ethylene, propylene, isobutene, acetaldehyde, acetic acid, ethyl acetate, methyl(meth)acrylate, ethyl-t-butyl ether ethylene glycol, ester composition, polyester, acrylic acid, aminohexanoic acid, diethyl carbonate, polyethylene (PE), polyethylene terephthalate (PET), polypropylene (PP), polyisobutylene, polymethylmethacrylate (PMMA), ethylene propylene diene rubber (EPDM), polybutylene terephthalate (PBT), polyethylene furanate (PEF), polyurethane (PU), and the like. Hereinafter, a method for synthesizing butadiene using ethanol as a raw material and a method for producing polyethylene and polyester of the present invention will be described by way of example, but it is needless to say that they can also be used for other chemical products and polymer raw materials.

<Method for Synthesizing Butadiene>

Butadiene is produced mainly by refining C4 fraction produced as a by-product in the synthesis of ethylene from petroleum (i.e., naphtha cracking) and is used as a raw material for synthetic rubber. However, recently there has been a desire for a technology for converting ethanol not derived from fossil fuels (ethanol derived from microbial fermentation) into 1,3-butadiene in place of the chemical industrial raw material obtained from petroleum. As a method for synthesizing butadiene using ethanol derived from microbial fermentation as a raw material, there are known a method using MgO as a catalyst, a method using a mixture of $Al_2O_3$ and ZnO, a catalyst having a magnesium silicate structure, and the like. As the catalyst, vanadium, manganese, iron, cobalt, nickel, copper, zinc, gallium, niobium, silver, indium, cerium, and the like are used other than those described above.

When the ethanol of the present invention is brought into contact with the above-mentioned catalyst and heated, an ethanol conversion reaction occurs, whereby 1,3-butadiene can be synthesized. By synthesizing butadiene using the ethanol of the present invention as a raw material, it is possible to realize an ultimate resource-recycling society that does not rely on petroleum resources.

The heating temperature for allowing the conversion reaction to proceed is such that the temperature in the reaction system is, for example, 300 to 450° C., preferably 350 to 400° C. When the temperature in the reaction system is lower than the above range, there is a tendency that the catalytic activity cannot be sufficiently obtained, the reaction rate decreases and thus the production efficiency decreases. On the other hand, when the temperature in the reaction system is higher than the above range, there is a possibility that the catalyst is easily deteriorated.

The reaction can be carried out by a conventional method such as batch, semi-batch, continuous or the like. The conversion rate of ethanol can be increased when the batch or semi-batch system is employed, but when the ethanol according to the present invention is employed, ethanol can be converted more efficiently than in the prior art even if the continuous system is employed. Although the reason for this is not clear, it is considered that ethanol derived from a recycling type resource having as a substrate a gas comprising carbon monoxide and hydrogen as described in the present invention has a characteristic peak which is not observed in ethanol derived from fossil fuel in a gas chromatograph measured by gas chromatography mass spectrometry.

Examples of the method for bringing the raw material into contact with the catalyst include a suspension bed system, a fluidized bed system, a fixed bed system, and the like. Further, either a vapor phase method or a liquid phase method may be used. It is preferable to use an immobilized bed gas-phase continuous flow reactor in which the catalyst is filled in a reaction tube to form a catalyst layer and the raw material is circulated as a gas to react in the vapor phase, from the viewpoint of easy recovery and regeneration of the catalyst. When the reaction is carried out in the vapor phase, the ethanol of the present invention may be supplied to the reactor without being gasified and diluted, or the ethanol may be appropriately diluted with an inert gas such as nitrogen, helium, argon or carbon dioxide and supplied to the reactor.

After the conversion reaction of ethanol has completed, the reaction product (1,3-butadiene) can be separated and purified by separation means such as filtration, concentration, distillation, extraction, or the like, or by separation means obtained by combining these separation means.

<Polyethylene>

Ethanol according to the present invention can also be suitably used as a raw material for polyethylene which is widely used as a general-purpose plastic. Conventional polyethylene is produced by synthesizing ethylene from petroleum and polymerizing ethylene monomers. By manufacturing polyethylene using the ethanol of the present invention, it is possible to realize an ultimate resource recycling society that does not rely on petroleum resources.

First, using the ethanol according to the present invention as a raw material, ethylene is synthesized which is a raw material for polyethylene. The method for manufacturing ethylene is not particularly limited and can be obtained by a conventionally known method, and as one example, ethylene can be obtained by dehydration reaction of ethanol. When ethylene is obtained by dehydration reaction of ethanol, a catalyst is usually used, and this catalyst for use can be a conventionally known catalyst with no particular limitation. An advantageous process is a fixed-bed flow reaction in which the catalyst and the product are easily separated, and γ-alumina or the like is preferable.

Since the dehydration reaction is an endothermic reaction, it is usually conducted under heating conditions. If the reaction proceeds at a commercially useful reaction rate, the heating temperature is not limited, but a temperature of 100° C. or higher, more preferably 250° C. or higher, and further preferably 300° C. or higher is suitable. The upper limit is not particularly limited, but is preferably 500° C. or lower, and more preferably 400° C. or lower from the viewpoint of energy balance and equipment.

The reaction pressure is not particularly limited, but a pressure of at least normal pressure is preferable in order to facilitate subsequent gas-liquid separation. Industrially, a fixed-bed flow reaction in which the catalyst can be easily separated is suitable, but a liquid-phase suspension bed, a fluidized bed and the like may be used.

In the ethanol dehydration reaction, the yield of reaction is influenced by the amount of water contained in ethanol supplied as a raw material. In general, when the dehydration reaction is carried out, it is preferable that there is no water, considering the removal efficiency of water. However, in the case of the dehydration reaction of ethanol using a solid catalyst, the amount of formation of other olefins, especially butene, tends to increase when there is no water. The lower limit of the allowable water content is 0.1% by mass or more, preferably 0.5% by mass or more. The upper limit is not particularly limited, but from the viewpoints of material balance and heat balance, it is preferably 50% by mass or less, more preferably 30% by mass or less, and further preferably 20% by mass or less.

By performing the ethanol dehydration reaction as described above, a mixture of ethylene, water, and a small amount of unreacted ethanol can be obtained. However, since ethylene is a gas at about 5 MPa or less at room temperature, ethylene can be obtained by gas-liquid separation from the mixture, except for water and ethanol. This method may be carried out by a known method. Subsequently, the ethylene obtained by the gas-liquid separation is further distilled, and there are no particular restrictions on the distillation method, operating temperature, residence time and the like, except that the operating pressure at this time is not less than normal pressure.

In the case of ethanol derived from a recycling type resource using a gas comprising carbon monoxide and hydrogen as a substrate as in the present invention, there is a characteristic peak which is not observed in ethanol derived from fossil fuels in gas chromatography measured by gas chromatography-mass spectrometry. Therefore, it is considered that ethylene obtained from ethanol contains an extremely small amount of impurities. Depending on the application of ethylene, these extremely small amounts of impurities may become a problem and may be removed by purification. The purification method is not particularly limited and can be carried out by a method known in the art. As a suitable purification procedure, an adsorption purification method can be exemplified. The adsorbent to be used is not particularly limited, and conventionally known adsorbents can be used. For example, a caustic water treatment may be used in combination as a method for purifying impurities in ethylene. In the case of caustic water treatment, it is desirable to perform the treatment before the adsorption purification. In this case, it is necessary to perform the water removal treatment after the caustic treatment and before the adsorption purification.

A method for polymerizing a monomer containing ethylene is not particularly limited, and the polymerization can be carried out by a conventionally known method. The polymerization temperature and polymerization pressure may be appropriately adjusted according to the polymerization method and the polymerization apparatus. The polymerization apparatus is not particularly limited, and conventionally known apparatuses can be used. Hereinafter, one example of a polymerization method for a monomer containing ethylene will be described.

The polymerization method for polyolefins, particularly ethylene polymers and copolymers of ethylene and α-olefins, can be appropriately selected depending on the type of polyethylene to be obtained, for example, the difference in density and branching of high-density polyethylene (HDPE), medium-density polyethylene (MDPE), low-density polyethylene (LDPE), and linear low-density polyethylene (LLDPE). For example, it is preferable to use a multisite catalyst such as a Ziegler-Natta catalyst or a singlesite catalyst such as a metallocene catalyst as the polymerization catalyst, and to carry out the polymerization in one stage or two or more stages by any of gas phase polymerization, slurry polymerization, solution polymerization, and high-pressure ion polymerization.

The single-site catalyst is a catalyst capable of forming a uniform active species, and is usually prepared by bringing a metallocene transition metal compound or a non-metallocene transition metal compound into contact with an activation co-catalyst. The single-site catalyst has a more uniform active site structure than the multithe multi-site catalyst, it is preferable that a polymer having a high molecular weight and a high uniformity can be polymerized. A metallocene catalyst is particularly preferable as the single-site catalyst. The metallocene catalyst is a catalyst comprising a transition metal compound of Group IV of the Periodic Table containing a ligand having a cyclopentadienyl skeleton, a co-catalyst, an organometallic compound if necessary, and each catalyst component of the carrier.

In a transition metal compound of Group IV of the Periodic Table containing a ligand having a cyclopentadienyl skeleton, the cyclopentadienyl skeleton is a cyclopentadienyl group, a substituted cyclopentadienyl group or the like. The substituted cyclopentadienyl group has a substituent such as a hydrocarbon group having 1 to 30 carbon atoms. Examples of the transition metal include zirconium, titanium, hafnium, and the like, with zirconium and hafnium being particularly preferred. It is preferable that the transition metal compound has two ligands having a cyclopentadienyl skeleton, and that each ligand having a cyclopentadienyl skeleton is bonded to each other by a cross-linking group. One or two or more of the above-mentioned transition metal compound a mixture can be made as a catalyst component.

The promoter can be referred to as those that make the transition metal compound described above effectively as a polymerization catalyst, or those that can equalize the ionic charge in a catalytically activated state. Examples of the promoter include benzene-soluble aluminoxane of an organoaluminum oxy compound, benzene-insoluble organoaluminum oxy compound, ion-exchangeable layered silicate, boron compound, ionic compound consisting of a cation containing or not containing an active hydrogen group and a non-coordinating anion, lanthanoid salts such as lanthanum oxide, tin oxide, phenoxy compound containing a fluoro group, and the like.

The transition metal compound described above may be used by being supported on a carrier of an inorganic or an organic compound. As the carrier, a porous oxide of an inorganic or an organic compound is preferable, and specific examples include an ion-exchangeable layered silicate such as montmorillonite, $SiO_2$, $Al_2O_3$, MgO, $ZrO_2$, $TiO_2$, $B_2O_3$, CaO, ZnO, BaO, $ThO_2$, and the like, or a mixture thereof.

Examples of the organometallic compound which may be used if necessary include an organoaluminum compound, organomagnesium compound, organozinc compound and the like. Of these, organoaluminum compound is preferably used.

As the polyolefin, a polymer of ethylene or a copolymer of ethylene and α-olefin may be used alone or as a mixture using two or more.

<Acetaldehyde>

Acetaldehyde is an important chemical as an industrial raw material. Acetaldehyde is useful as a raw material for acetic acid and ethyl acetate, for example.

Acetaldehyde can be produced by oxidizing ethanol by conventionally known methods. For example, ethanol can be oxidized with chlorine to give acetaldehyde. Chlorine usually reacts with ethanol in a gaseous state. Chlorine may be supplied at a concentration of approximately 100% or diluted with an inert gas (e.g., nitrogen, helium, neon, argon, etc.). In this case, the amount of dilution is 50% by weight or less, preferably 25% by weight or less in consideration of the reaction efficiency. It is preferable that ethanol and chlorine are reacted with 100 g of an aqueous ethanol solution at a feed rate of 25 to 100 sccm, for example.

The oxidation of ethanol by chlorine is preferably carried out using chlorine-containing compounds such as chlorine gas, hydrogen chloride, phosphorus pentachloride, phosphorus trichloride, phosphorus oxychloride, thionyl chloride, and hypochlorous acid compounds. This oxidation can be accomplished by, for example, photoreaction, thermal reaction, catalytic reaction, and the like. Among these, photochlorination of ethanol by chlorine gas and oxidation by thermal chlorination are preferable, and more preferably oxidation by photochlorination by chlorine gas. Examples of the photoreaction include a method of irradiating light of various wavelengths such as ultraviolet rays and visible light, and among these, it is preferable to irradiate light from a light source having a wavelength of about 300 to 500 nm to cause a reaction. The light source is not particularly limited, and fluorescent lamps, mercury lamps, halogen lamps, xenon lamps, metal halide lamps, excimer lamps, LED lamps, and the like can be used. The suitable reaction temperature is about 0 to 80° C., preferably about 0 to 50° C. The suitable reaction time is about 1 to 5 hours.

As another example, ethanol can be oxidized in the gas phase in the presence of oxygen molecules and a catalyst to produce acetaldehyde. For example, a base metal oxide in which gold fine particles are dispersed and fixed can be used as such a catalyst. Examples of the base metal oxide include $La_2O_3$, $MoO_3$, $Bi_2O_3$, SrO, $Y_2O_3$, MgO, BaO, $WO_3$, CuO, and a composite oxide containing one or more of them.

The ethanol oxidation reaction is carried out by bringing a gas containing ethanol and oxygen molecules into contact with the catalyst at, for example, 100 to 280° C. The oxygen molecules used in the reaction may be supplied as oxygen gas or air may be used. In addition, the raw material gas which is the gas may contain a dilution gas (carrier gas) if necessary. In this case, the apparatus used for the reaction may be a general apparatus which is usually used for performing a gas phase reaction. For example, the reaction may be carried out by filling a reaction tube with a catalyst, feeding a gas containing ethanol and oxygen gas or air into the reaction tube while the reaction tube is in a heated state to a predetermined temperature, bringing the raw material gas into contact with the catalyst, and recovering the reaction gas. The reaction may be carried out at atmospheric pressure and, if necessary, a pressure of about 0.5 to 5 Pa (atmospheric pressure) may be applied. As the diluent gas, for example, a so-called inert gas such as nitrogen, argon, helium or carbon dioxide is used. The amount of the diluent gas to be used may be appropriately determined in consideration of the composition, flow rate, reaction heat and the like of the raw material gas, but is preferably 1 to 100 times by volume with respect to ethanol.

The proportion of ethanol and oxygen molecules (oxygen gas) supplied to the reaction tube is not particularly limited, but is usually 0.5 to 100% by volume of oxygen gas or oxygen gas in air, preferably 1 to 10% by volume, and more preferably 2 to 5% by volume, with respect to ethanol. The amount of catalyst used is not particularly limited, but may generally be about 0.1 to 1.0 g when the inner diameter of the reaction tube is 6 to 10 mm. In practice, it is preferable to use an amount such that the space velocity (SV) is in the range of about 10,000 to 40,000 $hr^{-1} \cdot ml \cdot g_{cat}-1$ in relation to the gas flow rate.

Furthermore, acetaldehyde can be manufactured by dehydrogenating ethanol in the presence of a catalyst. For example, a solid catalyst containing copper as an active species can be used as such a catalyst. Copper as an active species may be in a form having an activity to convert ethanol into acetaldehyde, and may be in any form of metal copper (single substance), copper compounds (oxides, hydroxides, copper salts (inorganic acid salts such as copper sulfate, copper phosphate, copper nitrate, copper carbonate; organic acid salts such as copper salts of carboxylic acids), etc.). The solid catalyst may contain at least one selected from such a copper single substance and a copper compound. The copper as an active species is preferably in the form of metallic copper. In addition, the copper may be used in the form of metallic copper or a copper compound as it is or in the form of being supported on a carrier. The copper as an active species may act as a main catalyst of the solid catalyst and may be used in combination with a co-catalyst or the like. Further, the solid catalyst may be in a form in which both the copper and the co-catalyst are supported on a carrier.

The dehydrogenation reaction may be a liquid phase reaction as long as ethanol can be brought into contact with the solid catalyst, but it is usually a gas phase reaction in which gaseous ethanol and the solid catalyst are brought into contact in the gas phase. From the viewpoints of the equilibrium relationship between ethanol and acetaldehyde, the catalyst life, and the like, the reaction temperature may be 150 to 350° C., preferably 170 to 300° C., and further preferably 200 to 280° C. The higher the reaction temperature is, the more the equilibrium shifts to the acetaldehyde side, so that the conversion can be improved. The reaction may be carried out under pressure, but from the viewpoint of convenience, it may be carried out under atmospheric pressure. The reaction may also be carried out under reduced pressure from the viewpoint of advantageous ethanol conversion.

<Acetic Acid>

Acetic acid is an important chemical as an industrial raw material. Acetic acid is useful as a raw material for vinyl acetate monomer, acetic anhydride, acetic ester, and the like, for example.

Acetic acid can be produced by the oxidation of acetaldehyde by conventionally known methods in the art. For example, acetic acid can be produced by air oxidation of acetaldehyde in the presence of a catalyst. The catalyst includes manganese acetate and cobalt acetate.

<Ethyl-t-Butyl Ether>

Ethyl-t-butyl ether (ETBE) is an important chemical as an industrial raw material. ETBE is useful, for example, as an alternative fuel to gasoline, especially as a high-octane fuel.

ETBE can be synthesized from ethanol and isobutene by conventionally known methods. For example, ETBE can be produced by the reaction of ethanol and isobutene in the presence of a reaction catalyst. The molar ratio of isobutene to ethanol of the raw material is preferably from 0.1 to 10 mol, more preferably from 0.5 to 2 mol.

A cation exchange resin is preferably used as the reaction catalyst, and a strongly acidic cation exchange resin is more preferably used. As the strongly acidic cation exchange resin, a porous type (MR type) styrene resin is preferable, into which a strong acid group such as a sulfonic acid group ($-SO_3H$) is introduced as an ion exchange group. The particle size of the strongly acidic cation exchange resin is preferably 0.5 to 1.0 mm. The amount of reaction catalyst used is preferably 1 to 90 g, more preferably 1 to 90 g, and further preferably 4 to 9 g per mole of ethanol.

The method of using the reaction catalyst is not particularly limited, and it can be used for the reaction in the state of a fixed bed, a fluidized bed, or a suspended bed. The method of reacting isobutene with ethanol is not particularly limited, and it is preferable to carry out the reaction by a pressurized gas-liquid mixed phase reaction method in which ethanol can retain the liquid phase. In this case, the yield of ETBE obtained is further improved.

<Ester>

A wide variety of esters can be synthesized by reacting ethanol with various carboxylic acids. For example, ethyl benzoate can be obtained from ethanol and benzoic acid, and diethylene glycol, which is a raw material for polyester, can be obtained from ethanol via ethylene. By producing polyethylene using the ethanol of the present invention, it is possible to realize an ultimate resource recycling society that does not rely on petroleum resources.

The polyester comprises a diol unit and a dicarboxylic acid unit, and is obtained by a polycondensation reaction using ethylene glycol as the diol unit and terephthalic acid, isophthalic acid, or the like as the dicarboxylic acid unit. Ethylene glycol is derived from the ethanol of the present invention as a raw material, and for example, ethylene glycol can be obtained from ethanol by a method known in the art, a method for producing ethylene glycol via ethylene oxide, or the like.

As the dicarboxylic acid, aromatic dicarboxylic acid, aliphatic dicarboxylic acid and derivatives thereof can be used without limitation. Examples of the aromatic dicarboxylic acid include terephthalic acid, isophthalic acid and the like, and examples of the aromatic dicarboxylic acid derivatives include lower alkyl esters of aromatic dicarboxylic acid, specifically, methyl ester, ethyl ester, propyl ester and butyl ester. Among these, terephthalic acid is preferable, and as the aromatic dicarboxylic acid derivative, dimethyl terephthalate is preferable. Specific examples of the aliphatic dicarboxylic acid include chain or alicyclic dicarboxylic acid having 2 to 40 carbon atoms, such as oxalic acid, succinic acid, glutaric acid, adipic acid, sebacic acid, dodecanedioic acid, dimer acid, and cyclohexane dicarboxylic acid. Specific examples of the aliphatic dicarboxylic acid derivatives include lower alkyl ester such as methyl ester, ethyl ester, propyl ester and butyl ester of the aliphatic dicarboxylic acid, and cyclic acid anhydrides of the aliphatic dicarboxylic acid such as succinic anhydride. Among these, adipic acid, succinic acid, dimer acid or a mixture thereof are preferable, and those containing succinic acid as a main component are particularly preferable. As the aliphatic dicarboxylic acid derivative, more preferred are methyl ester of adipic acid and succinic acid or a mixture thereof.

Polyester can be obtained by a conventionally known method in which the diol unit and the dicarboxylic acid unit are subjected to polycondensation. Specifically, polyester can be produced by a general method of melt polymerization in which an esterification reaction and/or an transesterification reaction between the dicarboxylic acid component and the diol component is carried out, followed by a polycondensation reaction under reduced pressure, or by a known method of solution heating dehydration condensation using an organic solvent.

The polycondensation reaction is preferably carried out in the presence of a polymerization catalyst, and examples of the polymerization catalyst include a titanium compound, zirconium compound, germanium compound and the like.

The reaction temperature of the esterification reaction and/or the transesterification reaction between the dicarboxylic acid component and the diol component is usually in the range of 150 to 260° C., and the reaction atmosphere is usually an inert gas atmosphere such as nitrogen or argon.

In the polycondensation reaction step, a chain extender (coupling agent) may be added to the reaction system. After the polycondensation is completed, the chain extender is added to the reaction system in a uniformly molten state without a solvent, and is reacted with the polyester obtained by the polycondensation.

After the obtained polyester is solidified, solid phase polymerization may be carried out, if necessary, in order to further increase the degree of polymerization or to remove oligomers such as cyclic trimers.

Various additives may be added in the manufacturing process of polyester within a range in which the properties thereof are not impaired, and for example, plasticizers, ultraviolet stabilizers, coloring inhibitors, matting agents, deodorants, flame retardants, weathering agents, antistatic agents, friction reducing agents, demolding agents, antioxidants, ion exchangers, coloring pigments, and the like may be added.

Ethanol according to the present invention is not limited to the above-mentioned polymers and can be used as a raw material for various other polymers, and since the molded product of the obtained polymer is a carbon-neutral material, it is possible to realize an ultimate resource recycling society that is not dependent on petroleum resources.

<Product Containing Ethanol>

Ethanol according to the present invention can be used not only as a polymer raw material as described above but also in various products. Examples of products include chemical products such as cosmetics, perfumes, fuels, antifreeze solutions, disinfectants, disinfectants, cleaners, mold removers, detergents, shampoo, soaps, antiperspirants, face wash sheets, solvents, coatings, adhesives, diluents, food additives, and the like. By using these products in these applications, it is possible to exhibit an appropriate effect according to the application.

<Fuel>

Ethanol according to the present invention can also be used as a raw material for fuel (for example, jet fuel, kerosene, light oil, gasoline) and the like. Because ethanol has high germicidal activity, it can also function as a germicide for preventing bacteria growth of bacteria and the like in fuel systems such as engines and pipes.

According to the Japanese Society of Automotive Engineers Standards (2006), the concentration of ethanol in fuel ethanol is prescribed as 99.5 volume % or more. In other countries (e.g., India), the concentration of ethanol in fuel ethanol is prescribed as 99.5 volume % or more. Accordingly, ethanol with a purity of 99.5 to 99.9 volume % can be suitably used for ethanol-only vehicles. Since fuel ethanol can be used for purposes other than ethanol-only vehicles, ethanol with a purity of 99.5 to 99.9 volume % has particularly high versatility.

The ethanol according to the invention can also be mixed with gasoline and used as an ethanol-blended gasoline. By using ethanol-blended gasoline, the environmental burden can be reduced. Ethanol used in the ethanol-blended gasoline has a purity of 92.0% by volume or more, preferably $^9$5.0% by volume or more, further preferably 99.5% by volume or more.

The ethanol content in the ethanol-blended gasoline is preferably from 1% by volume to 15% by volume, more preferably from 2% by volume to 12% by volume, and further preferably from 3% by volume to 10% by volume. When the ethanol content is 1% by volume or more, it is possible to attain the advantage that the octane number improves by blending ethanol, and when it is 15% by volume or less, the evaporation characteristic does not significantly change due to the occurrence of azeotrope with another gasoline substrate, thereby ensuring proper operability of a gasoline vehicle.

The water content in the ethanol-blended gasoline is preferably 0.01 to 0.9 mass %, and more preferably 0.01 to 0.7 mass %. The lower limit of water content depends on the saturated water content of the gasoline substrate and the water content in the ethanol, but is substantially about 0.01 mass %. If the upper limit is 0.9 mass % or less, phase separation can be prevented, and even in the case of phase separation, the gasoline layer enables proper operation of the gasoline engine. The water content can be measured by "Crude oil and petroleum products—water content test method" described in JIS K 2275, and for example, Karl Fischer coulometric titration can be used.

As the gasoline substrate, a commonly used gasoline substrate can be optionally used, and there is no particular limitation. Examples of the gasoline substrate include light naphtha obtained by atmospheric distillation of crude oil, preferably desulfurized light naphtha obtained by desulfurization thereof, catalytic reformed gasoline obtained by catalytic reforming of heavy naphtha after desulfurization thereof, debenzene catalytic reformed gasoline obtained by debenzene treatment thereof, debenzene light catalytic reformed gasoline, debenzene heavy catalytic reformed gasoline, and mixtures thereof, cracked gasoline obtained by catalytic cracking or hydrogenolysis methods, light cracked gasoline, heavy cracked gasoline, and mixtures thereof, and isomerized gasoline obtained by isomerization of light naphtha.

Furthermore, the ethanol-based ETBE according to the invention can be mixed with gasoline and used as an ETBE-blended gasoline. The environmental burden can be reduced by using the ETBE-blended gasoline. The ETBE content of the ETBE-blended gasoline is preferably from 1% by volume to 15% by volume, more preferably from 2% by volume to 12% by volume, and further preferably from 3% by volume to 10% by volume. When the ETBE content is 1% by volume or more, the advantage of improving the octane number by blending ETBE can be obtained, and when the ETBE content is 15% by volume or less, the evaporation characteristics do not significantly change due to the occurrence of azeotrope with another gasoline substrate, thereby ensuring proper operability of a gasoline vehicle.

EXAMPLES

Hereinafter, the present invention will be described in more details with reference to the examples, but the present invention shall not be limited to the following examples as long as the gist of the invention is not deviated.

Example A

<Ethanol Component Evaluation Method>
In the following Examples and Comparative Examples, the components of ethanol were evaluated by analysis using an odor sniffing gas chromatograph mass spectrometer (JMS-Q1050GC Ultra Quad GC/MS manufactured by Nihon Denshi Co., Ltd.). The measurement conditions were as follows.
<Analysis Conditions of the GC/MS Method>
  Column: DB-WAX (60 m in length, 0.25 mm in inner diameter, 0.25 μm in film thickness)
  Oven temperature: 40° C., 1 minute→5° C./min→100° C., 10 minutes→10° C./min→250° C., 4 minutes
  Sampling time: 5 minutes
  Carrier gas: He (3.0 mL/min)
<Butadiene Quantitative Method>
Quantitative evaluation of butadiene was carried out by analysis using a gas chromatography apparatus (GC-2014, manufactured by SHIMADZU). The measurement conditions were as follows.
<Analysis Conditions of GC/MS Method>
  Column: Rt-Q-BOND (length 30 m, inner diameter 0.32 mm, film thickness 10 μm)
  Oven temperature: 60° C., 11.5 minutes→10° C./min→100° C., 14.5 minutes→10° C./min→250° C.;
  Sampling time: 5 minutes;
  Carrier gas: He (30 cm/s);
  Split ratio: 75
<Ethyl Benzoate Determination Method>
Quantitative evaluation of ethyl benzoate was performed by analysis using a gas chromatography apparatus. The measurement conditions were as follows.
<Analysis Conditions of the GC/MS Method>
  Column: DB-1 (length 30.0 m, inner diameter 0.254 mm, film thickness 0.25 m)
  Heating condition: 30° C.-300° C. 15° C./min
  Carrier gas: He 100 kPa
  Split ratio: 50
<Combustion Efficiency Quantification Method>
Quantitative evaluation of combustion efficiency of ethanol was carried out by total heat generation analysis using a cone calorimeter manufactured by FTT.

Example A1

<Preparation of Ethanol>
Ethanol was prepared as follows.
(Raw Material Gas Generation Step)
Gas discharged after combustion of general waste in a waste incineration facility was used. The raw material gas consisted of about 30% by volume of carbon monoxide, about 30% by volume of carbon dioxide, about 30% by volume of hydrogen and about 10% by volume of nitrogen.
(Synthetic Gas Purification Step)
Using a PSA device, which is an impurity removing apparatus for the raw material gas produced as described above, carbon dioxide contained in the synthetic gas was removed so that the content will be 60 to 80% by volume of the original content (about 30% by volume) under conditions in which the gas temperature was heated to 80° C., followed by re-cooling using a double-tube-type heat exchanger using steam at 150° C. by using a double-tube-type heat exchanger using temperature increase of gas and cooling water at 25° C. to precipitate impurities and remove the precipitated impurities with a filter, thereby giving a synthetic gas.
(Microbial Fermentation Step)
The synthetic gas thus obtained was continuously supplied to a continuous fermentation apparatus (microbial fermentation tank) equipped with a main reactor, a synthetic gas supply hole, and a discharge hole, which was packed with a seed of *Clostridium autoethanogenum* (microorganism) and a liquid medium for culturing the microorganism (containing an appropriate amount of phosphorus compounds, nitrogen compounds, various minerals, and the like), and culture (microbial fermentation) was carried out continuously for 300 hours. Thereafter, about 8000 L of a culture solution containing ethanol was extracted from the discharge hole.
(Separation Step)
The culture solution obtained in the fermentation step was used in a solid-liquid separation filter device to obtain an ethanol-containing liquid under conditions of a culture solution introduction pressure of 200 kPa or more.
(Distillation Process)
Subsequently, the ethanol-containing liquid was introduced into a distillation apparatus equipped with a heater using steam at 170° C. After the temperature at the distillation column bottom was raised to 101° C. within 8 to 15 minutes, the ethanol-containing liquid was introduced from the middle of the distillation column, and during continuous operation, purified ethanol was obtained by continuous operation under the conditions of 15 seconds/L, at 101° C. at the bottom, 99° C. at the middle, and 91° C. at the top.

(Ethanol Component Evaluation)

The results of gas chromatographic analysis for ethanol obtained as described above were as shown in FIG. 1A.

(Production Method of Butadiene)

Butadiene was produced using the ethanol obtained as described above. First, the ethanol obtained was vaporized by passing it through a single tube heated to 90° C. in order to prepare a gas to be used for the reaction, and the vaporized ethanol gas was combined with nitrogen. At this time, mass flow was used to control the flow rate of ethanol gas to SV360 L/hr/L, and nitrogen to SV840 L/hr/L, thereby obtaining a mixed gas of 30% by volume of ethanol (gas conversion) and 70% by volume of nitrogen (gas conversion). Subsequently, a stainless steel cylindrical reaction tube having a diameter of ½ inch (1.27 cm) and a length of 15.7 inch (40 cm) filled with 0.85 g of a butadiene synthesis catalyst mainly composed of Hf, Zn and Ce was continuously supplied with the mixed gas while maintaining the temperature of 350° C. and the pressure (pressure of the reaction bed) of 0.1 MPa, thereby obtaining a butadiene-containing gas. The butadiene-containing gas thus obtained was used for quantifying the butadiene content using a gas chromatography apparatus of GC-2014 (manufactured by SHIMADZU). The results were as shown in Table A1.

Comparative Example A1

Figure 1B:
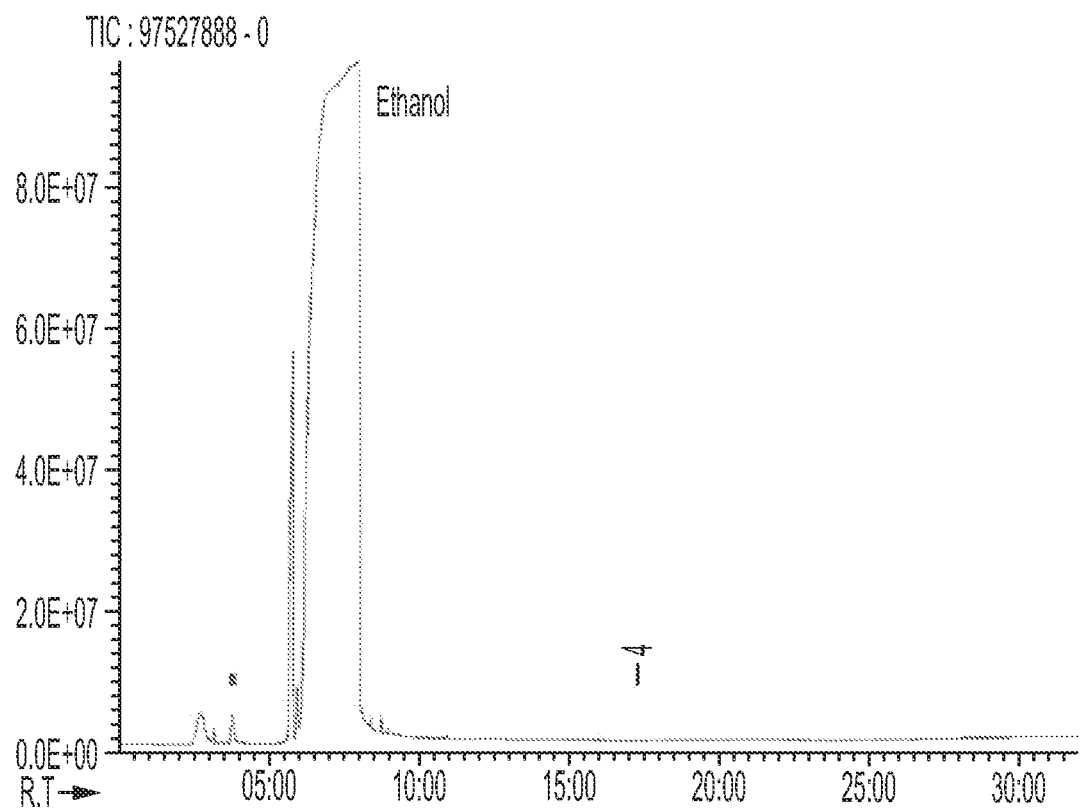
FIG. 1B is a gas chromatogram of ethanol used in Comparative Example A1.

Butadiene was produced by the same method as in Example A1 using 99 degrees ethanol (manufactured by Amakasu Chemical Industry Co., Ltd.) which is ethanol derived from fossil fuel, and the content of butadiene was determined in the same manner as in Example A1. The results were as shown in Table A1. The components of the ethanol used were evaluated in the same manner as in Example A1. The results of gas chromatographic analysis were as shown in FIG. 1B.

Comparative Example A2

Figure 1C:
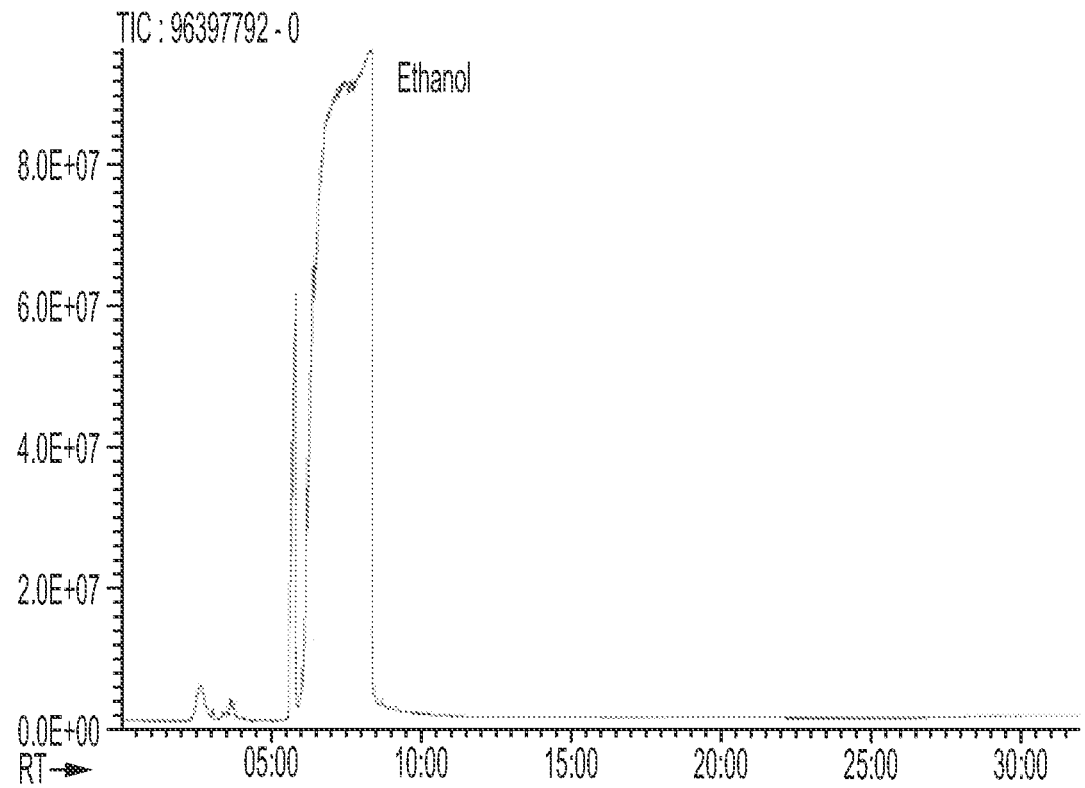
FIG. 1C is a gas chromatogram of ethanol used in Comparative Example A2.

Butadiene was manufactured by the same method as in Example A1 using 99 degrees ethanol (manufactured by Amakasu Chemical Industry Co., Ltd.) derived from the saccharification and fermentation of plants, and the content of butadiene was quantified in the same manner as in Example A1. The results were as shown in Table A1. The components of the ethanol used were evaluated in the same manner as in Example A1. The results of gas chromatographic analysis were as shown in FIG. 1C.

TABLE A1

Content of Butadiene

| | Ethanol | Content of Butadiene (%) |
|---|---|---|
| Ex. A1 | Derived from synthetic gas | 61.2 |
| Comp. Ex. A1 | Derived from fossil fuel | 57.2 |
| Comp. Ex. A2 | Derived from saccharification and fermentation | 57.5 |

As shown in Table A1, it has been found that ethanol produced using the gas discharged after burning general waste in a waste incineration facility has a higher conversion efficiency to butadiene than ethanol derived from conventional fossil fuels or ethanol derived from saccharification and fermentation from plants.

Example A2

(Production of Ethyl Benzoate)

Ethyl benzoate was produced using the same ethanol as that used in Example A1 in the following manner. First, 36.8 g of benzoic acid and 200 ml of ethanol were mixed under a stream of argon, 9 ml of concentrated sulfuric acid was added thereto, and the mixture was stirred under reflux for 5 hours. Thereafter, the mixture was allowed to cool to room temperature, unreacted ethanol was removed under reduced pressure, and ethyl benzoate synthesized with 100 ml of diethyl ether was recovered. The recovered solution was washed with distilled water, dried using magnesium sulfide, and then filtered and concentrated.

The obtained filtrate was subjected to component analysis using a gas chromatography apparatus, and the amount of ethyl benzoate synthesized was determined. The analytical conditions at this time are as follows. The analytical results are shown in Table A2.

Column: DB-1 (Length 30.0 m, Inner Diameter 0.254 mm, Film Thickness 0.25 m)
Heating condition: 30-300° C. 15° C./min
Carrier gas: He 100 kPa
Split ratio: 50

Comparative Example A3

Ethyl benzoate was manufactured and quantified in the same manner as in Example A2 except that ethanol derived from petrochemicals used in Comparative Example A1 was used. The analytical results were as shown in Table A2.

Comparative Example A4

Ethyl benzoate was manufactured and quantified in the same manner as in Example A2 except that ethanol derived from petrochemicals used in Comparative Example A2 was used. The analytical results were as shown in Table A2.

TABLE A2

Content of Ethyl benzoate

| | Ethanol | Content of Ethyl benzoate (%) |
|---|---|---|
| Ex. A1 | Derived from synthetic gas | 94.4 |
| Comp. Ex. A1 | Derived from fossil fuel | 93.2 |
| Comp. Ex. A2 | Derived from saccharification and fermentation | 93.4 |

As shown in Table A2, it has been found that ethanol produced using the gas discharged after burning general waste in a waste incineration facility has a higher conversion efficiency to ethyl benzoate than ethanol derived from conventional fossil fuels or ethanol derived from saccharification and fermentation from plants.

Example A3

The combustion efficiency of ethanol was quantified using the same ethanol as that used in Example 1. The fuel efficiency was quantified by adding 30 g of ethanol to a heat-resistant container which is 60 mm long×60 mm wide× 30 mm high under non-heating conditions, subsequently igniting, and measuring the amount of oxygen reduction until complete combustion in a cone calorimeter (manufactured by FTT), and calculating the total heat generation based on the amount of oxygen reduction. The quantitative results were as shown in Table A3.

Comparative Example A5

The combustion efficiency of ethanol was quantified in the same manner as in Example A3 except that ethanol used in Comparative Example A1 was used. The quantitative results were as shown in Table A3.

Comparative Example A6

The combustion efficiency of ethanol was quantified in the same manner as in Example A3 except that ethanol used in Comparative Example A2 was used. The quantitative results were as shown in Table A3.

TABLE A3

Combustion Efficiency

| Ethanol | | Combustion Efficiency (kw/kg) |
|---|---|---|
| Ex. A1 | Derived from synthetic gas | 7.78 |
| Comp. Ex. A1 | Derived from fossil fuel | 7.54 |
| Comp. Ex. A2 | Derived from saccharification and fermentation | 7.57 |

Example B

<Ethanol Component Evaluation Method>

In the following Examples and Comparative Examples, the component evaluation of ethanol was carried out using a gas chromatography apparatus (GC-2014, manufactured by SHIMADZU) GC/MS method. The measurement conditions were as follows.

<Analysis Conditions of the GC/MS Method>
  Column: DB-5MS (length 30 m, inner diameter 0.25 mm, film thickness 0.25 μm)
  Oven temperature: 40° C.→10° C./min→300° C.
  Carrier gas: He (1.28 mL/min)
  Inlet temperature: 300° C.
  Detector temperature: 300° C.
  Detector: Hydrogen flame ionization detector
  Injection volume: 1 μL (split ratio 1:20)

<Butadiene Quantitative Method>
Quantitative evaluation of butadiene was performed in the same manner as in Example A.

<Ethyl Benzoate Determination Method>
Quantitative evaluation of ethyl benzoate was performed in the same manner as in Example A.

<Combustion Efficiency Quantification Method>
Quantitative evaluation of ethanol combustion efficiency was performed in the same manner as in Example A.

Example B1

<Preparation of Ethanol>
Ethanol was prepared in the same manner as in Example A.

(Ethanol Component Evaluation)
With respect to the ethanol obtained as described above, the results of gas chromatographic analysis were as shown in FIGS. B1 and B2 (enlarged view). It was confirmed that the peak with a retention time of 12 minutes 30 seconds to 12 minutes 40 seconds was derived from n-tetradecane, because the retention time was in conformity with that of the sample of n-tetradecane (C14). The content of n-tetradecane in the ethanol thus obtained was 0.03 mg/L.

(Production Method of Butadiene)
Butadiene was manufactured in the same manner as in Example A using the ethanol obtained as described above. The content of butadiene in the gas containing butadiene thus obtained was quantified using a gas chromatography apparatus GC-2014 (manufactured by SHIMADZU). The results were as shown in Table B1.

Comparative Example B1

Figure 2A:
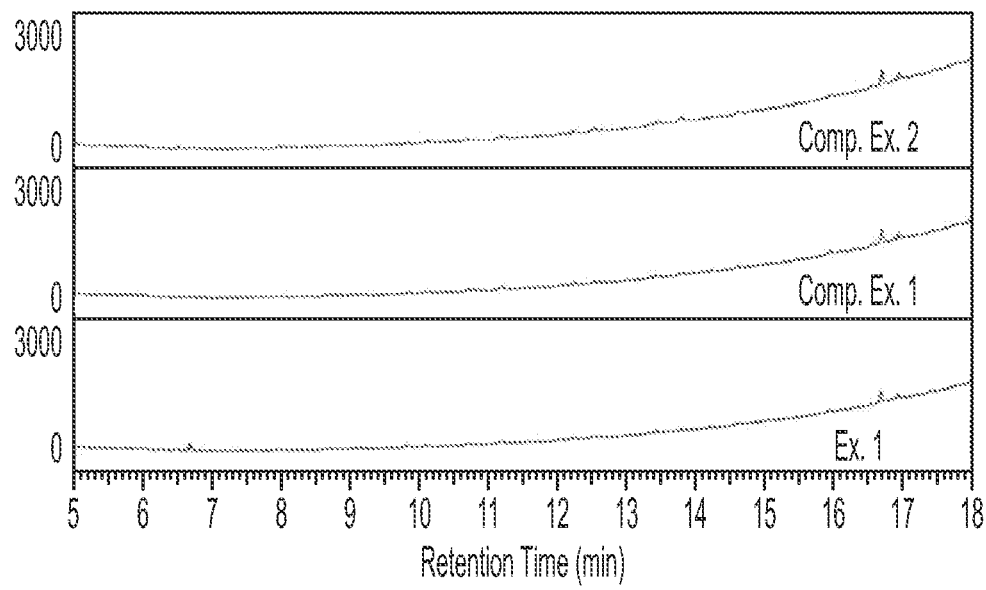
FIG. 2A is a gas chromatogram of ethanol used in Example B1 and Comparative Examples B1 and B2.
Figure 2B:
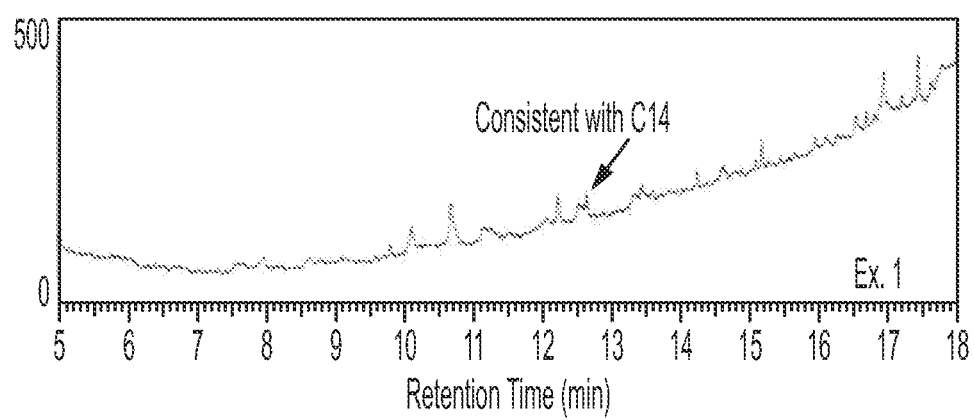
FIG. 2B is an enlarged view of the chromatogram of Example B1.

Butadiene was produced by the same method as in Example B1 using 99 degrees ethanol (manufactured by Amakasu Chemical Industry Co., Ltd.) which is ethanol derived from fossil fuel, and the content of butadiene was determined in the same manner as in Example B1. The results were as shown in Table B1. The components of ethanol used were evaluated in the same manner as in Example B1. The results of gas chromatographic analysis were as shown in FIG. 2A. In an enlarged view (not shown) of the gas chromatograph, no peak was detected with a retention time of 12 minutes 30 seconds to 12 minutes 40 seconds derived from n-tetradecane.

Comparative Example B2

Butadiene was manufactured by the same method as in Example B1 using 99 degrees ethanol (manufactured by Amakasu Chemical Industry Co., Ltd.) derived from the saccharification and fermentation of plants, and the content of butadiene was quantified in the same manner as in Example B1. The results were as shown in Table B1. The components of ethanol used were evaluated in the same manner as in Example B1. The results of gas chromatographic analysis were as shown in FIG. 2A. In an enlarged view (not shown) of the gas chromatograph, no peak was detected with a retention time of 12 minutes 30 seconds to 12 minutes 40 seconds derived from n-tetradecane.

TABLE B1

Butadiene Content

| | Ethanol | Butadiene Content (%) |
|---|---|---|
| Ex. B1 | Derived from synthetic gas | 61.2 |
| Comp. Ex. B1 | Derived from fossil fuel | 57.2 |
| Comp. Ex. B2 | Derived from saccharification and fermentation | 57.5 |

As shown in Table B1, it was found that ethanol manufactured using the gas discharged after burning general waste in a waste incineration facility has a higher conversion efficiency to butadiene than ethanol derived from conventional fossil fuels or ethanol derived from saccharification and fermentation from plants.

Example B2

(Manufacturing of Ethyl Benzoate)
Using the same ethanol as that used in Example A1, ethyl benzoate was produced in the same manner as in Example A, followed by component analysis using a gas chromatography apparatus to quantify the amount of ethyl benzoate synthesis. The analysis results were as shown in Table B2.

Comparative Example B3

Ethyl benzoate was manufactured and quantified in the same manner as in Example B2, except that ethanol derived from petrochemicals used in Comparative Example B1 was used. The analytical results were as shown in Table B2.

Comparative Example B4

Ethyl benzoate was manufactured and quantified in the same manner as in Example B2 except that ethanol derived from petrochemicals used in Comparative Example B2 was used. The analytical results were as shown in Table B2.

TABLE B2

Ethyl benzoate Content

| Ethanol | | Ethyl benzoate Content (%) |
|---|---|---|
| Ex. B1 | Derived from synthetic gas | 94.4 |
| Comp. Ex. B1 | Derived from fossil fuel | 93.2 |
| Comp. Ex. B2 | Derived from saccharification and fermentation | 93.4 |

As shown in Table B2, it has been found that ethanol produced using the gas discharged after burning general waste in a waste incineration facility has a higher conversion efficiency to ethyl benzoate than ethanol derived from conventional fossil fuels or ethanol derived from saccharification fermentation from plants.

Example B3

Ethanol combustion efficiency was quantified using the same ethanol as that used in Example B1. The fuel efficiency was quantified by adding 30 g of ethanol to a heat-resistant container of 60 mm in length×60 mm in width×30 mm in height under non-heating conditions, igniting, measuring the amount of oxygen reduction until complete combustion in a cone calorimeter (manufactured by FTT), and calculating the total heat generation based on the amount of oxygen reduction. The determination results were as shown in Table B3.

Comparative Example B5

The combustion efficiency of ethanol was quantified in the same manner as in Example B3 except that ethanol used in Comparative Example B1 was used. The quantitative results were as shown in Table B3.

Comparative Example B6

The combustion efficiency of ethanol was quantified in the same manner as in Example B3, except that ethanol used in Comparative Example B2 was used. The quantitative results were as shown in Table B3.

TABLE B3

Combustion Efficiency

| | Ethanol | Combustion Efficiency (kw/kg) |
|---|---|---|
| Ex. B1 | Derived from synthetic gas | 7.78 |
| Comp. Ex. B1 | Derived from fossil fuel | 7.54 |
| Comp. Ex. B2 | Derived from saccharification and fermentation | 7.57 |

Example C

<Ethanol Component Evaluation Method>
The ethanol component evaluation method was performed in the same manner as in Example A described above.
<Butadiene Quantitative Method>
Quantitative evaluation of butadiene was performed in the same manner as in Example A.
<Ethyl Benzoate Determination Method>
Quantitative evaluation of ethyl benzoate was performed in the same manner as in Example A.
<Combustion Efficiency Quantification Method>
Quantitative evaluation of ethanol combustion efficiency was performed in the same manner as in Example A.

Example C1

<Preparation of Ethanol>
Ethanol was prepared in the same manner as in Example A.
(Ethanol Component Evaluation)
The results of gas chromatographic analysis for ethanol obtained as described above were as shown in FIG. 3. The peak with a retention time of 6 minutes 36 seconds to 6 minutes 45 seconds was confirmed to be derived from n-decane because the retention time was in conformity with that of the sample of n-decane (C10). The content of n-decane in the obtained ethanol was 0.32 mg/L.
(Production Method of Butadiene)
Butadiene was produced in the same manner as in Example A using the ethanol obtained as described above. The content of butadiene in the gas containing butadiene thus obtained was determined using a gas chromatography apparatus GC-2014 (manufactured by SHIMADZU). The results were as shown in Table C1.

Comparative Example C1

Figure 3:
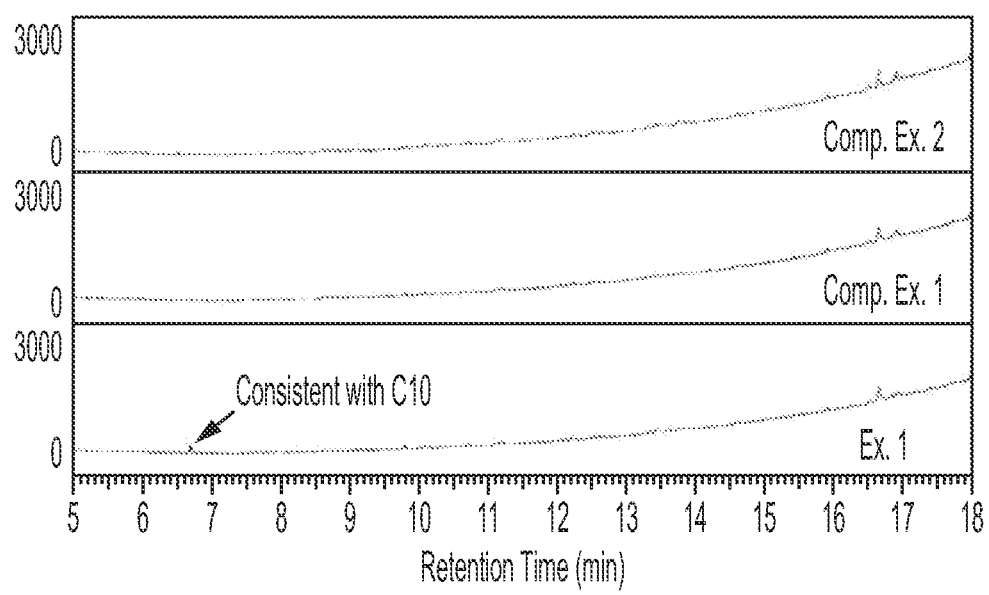
FIG. 3 is a gas chromatogram of ethanol used in Example C1 and Comparative Examples C1 and C2.

Butadiene was produced by the same method as in Example C1 using 99 degrees ethanol (manufactured by Amakasu Chemical Industry Co., Ltd.) which is ethanol derived from fossil fuel, and the content of butadiene was determined in the same manner as in Example C1. The results were as shown in Table C1. The components of ethanol used were evaluated in the same manner as in Example C1. The results of gas chromatographic analysis were as shown in FIG. 3. No peak was detected in the gas chromatograph with a retention time of 6 minutes 36 seconds to 6 minutes 45 seconds derived from n-decane.

Comparative Example C2

Butadiene was produced by the same method as in Example C1 using 99 degrees ethanol (manufactured by Amakasu Chemical Industry Co., Ltd.) derived from saccharification and fermentation of plants, and the content of butadiene was determined in the same manner as in Example C1. The results were as shown in Table C1. The components of ethanol used were evaluated in the same manner as in Example C1. The results of gas chromatographic analysis were as shown in FIG. 3. No peak was detected in the gas chromatograph with a retention time of 6 minutes 36 seconds to 6 minutes 45 seconds derived from n-decane.

TABLE C1

| | Butadiene Content | |
|---|---|---|
| | Ethanol | Butadiene Content (%) |
| Ex. C1 | Derived from synthetic gas | 61.2 |
| Comp. Ex. C1 | Derived from fossil fuel | 57.2 |
| Comp. Ex. C2 | Derived from saccharification and fermentation | 57.5 |

As shown in Table C1, it has been found that ethanol produced using the gas discharged after burning general waste in a waste incineration facility has a higher conversion efficiency to butadiene than ethanol derived from conventional fossil fuels or ethanol derived from saccharification fermentation from plants.

Example C2

(Production of Ethyl Benzoate)

Using the same ethanol as used in Example C1, ethyl benzoate was manufactured in the same manner as in Example A, followed by component analysis using a gas chromatography apparatus to quantify the amount of ethyl benzoate synthesis. The analytical results were as shown in Table C2.

Comparative Example C3

Ethyl benzoate was manufactured and quantified in the same manner as in Example C2 except that ethanol derived from petrochemicals used in Comparative Example C1 was used. The analytical results were as shown in Table C2.

Comparative Example C4

Ethyl benzoate was manufactured and quantified in the same manner as in Example C2 except that ethanol derived from petrochemicals used in Comparative Example C2 was used. The analytical results were as shown in Table C2.

TABLE C2

| | Ethyl Benzoate Content | |
|---|---|---|
| | Ethanol | Ethyl Benzoate Content (%) |
| Ex. C1 | Derived from synthetic gas | 94.4 |
| Comp. Ex. C1 | Derived from fossil fuel | 93.2 |
| Comp. Ex. C2 | Derived from saccharification and fermentation | 93.4 |

As shown in Table C2, it has been found that ethanol produced using the gas discharged after burning general waste in a waste incineration facility has a higher conversion efficiency to ethyl benzoate than ethanol derived from conventional fossil fuels or ethanol derived from saccharification fermentation from plants.

Example C3

The ethanol combustion efficiency was quantified using the same ethanol as that used in Example C1. The fuel efficiency was determined by adding 30 g of ethanol to a heat-resistant container with 60 mm in length×60 mm in width×30 mm in height under non-heating conditions, igniting the container, measuring the amount of oxygen reduction until complete combustion in a cone calorimeter (manufactured by FTT), and calculating the total heat generation based on the amount of oxygen reduction. The quantitative results were as shown in Table C3.

Comparative Example C5

The combustion efficiency of ethanol was quantified in the same manner as in Example C3, except that ethanol used in Comparative Example C1 was used. The quantitative results were as shown in Table C3.

Comparative Example C6

The combustion efficiency of ethanol was quantified in the same manner as in Example C3, except that ethanol used in Comparative Example C2 was used. The quantitative results were as shown in Table C3.

TABLE C3

| | Combustion Efficiency | |
|---|---|---|
| | Ethanol | Combustion Efficiency (kw/kg) |
| Ex. C1 | Derived from synthetic gas | 7.78 |
| Comp. Ex. C1 | Derived from fossil fuel | 7.54 |
| Comp. Ex. C2 | Derived from saccharification and fermentation | 7.57 |

Example D

<Ethanol Component Evaluation Method>

The ethanol component evaluation method was performed in the same manner as in Example A described above.

<Butadiene Quantitative Method>

Quantitative evaluation of butadiene was performed in the same manner as in Example A described above.

<Ethyl Benzoate Determination Method>

Quantitative evaluation of ethyl benzoate was performed in the same manner as in Example A described above.

<Combustion Efficiency Quantification Method>

Quantitative evaluation of ethanol combustion efficiency was performed in the same manner as in Example A described above.

Example D1

<Preparation of Ethanol>

Ethanol was prepared in the same manner as in Example A.

(Ethanol Component Evaluation)

With respect to the ethanol obtained as described above, the results of gas chromatographic analysis were as shown in FIGS. D1 and D2 (enlarged view). It was confirmed that the peak with a retention time of 15 minutes 00 seconds to 15 minutes 15 seconds was derived from n-hexadecane because the retention time was in conformity with that of the sample of n-hexadecane (C16). The content of n-hexadecane in the ethanol thus obtained was 0.05 mg/L.
(Production Method of Butadiene)

Butadiene was produced in the same manner as in Example B using the ethanol obtained as described above. The content of butadiene in the gas containing butadiene thus obtained was determined using a gas chromatography apparatus GC-2014 (manufactured by SHIMADZU). The results were as shown in Table D1.

Comparative Example D1

Figure 4A:
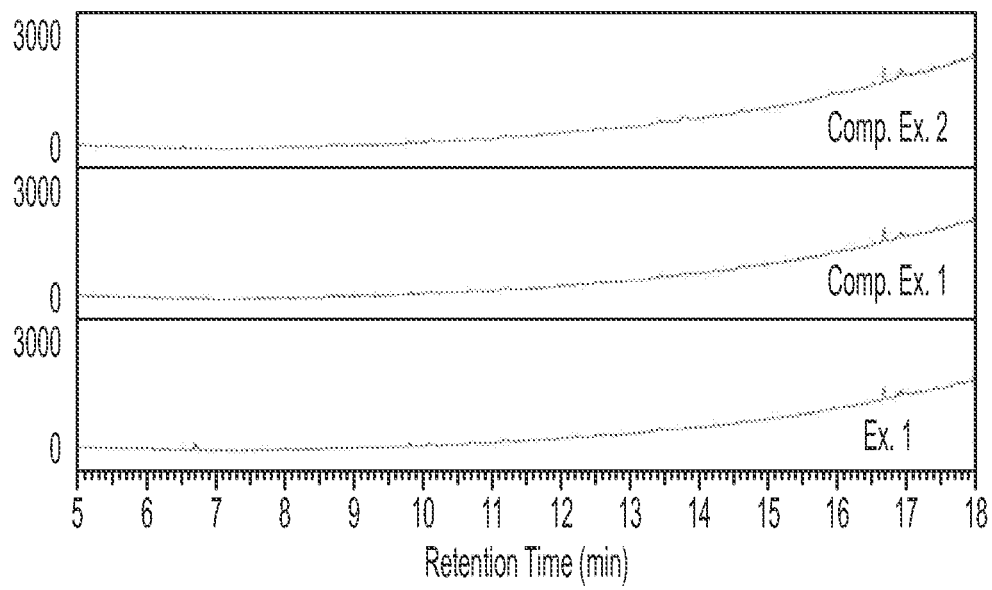
FIG. 4A is a gas chromatogram of ethanol used in Example D1 and Comparative Examples D1 and D2.
Figure 4B:
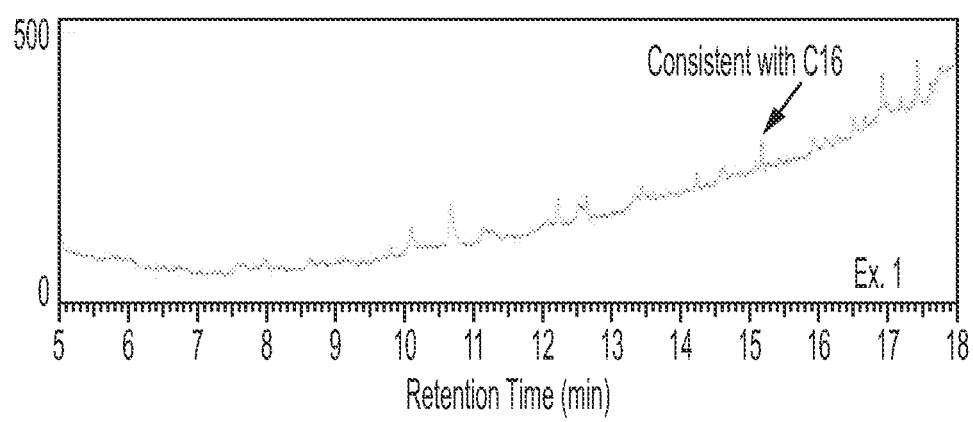
FIG. 4B is an enlarged view of the chromatogram of Example D1.

Butadiene was produced by the same method as in Example D1 using 99 degrees ethanol (manufactured by Amakasu Chemical Industry Co., Ltd.) which is ethanol derived from fossil fuel, and the content of butadiene was quantified in the same manner as in Example D1. The results were as shown in Table D1. The components of ethanol used were evaluated in the same manner as in Example D1. The results of gas chromatographic analysis were as shown in FIG. 4A. In an enlarged view (not shown) of the gas chromatograph, no peak was detected with a retention time of 15 minutes 00 seconds to 15 minutes 15 seconds derived from n-hexadecane.

Comparative Example D2

Butadiene was produced by the same method as in Example D1 using 99 degrees ethanol (manufactured by Amakasu Chemical Industry Co., Ltd.) derived from saccharification and fermentation of plants, and the content of butadiene was quantified in the same manner as in Example D1. The results were as shown in Table D1. The components of ethanol used were evaluated in the same manner as in Example D1. The results of gas chromatographic analysis were as shown in FIG. 4A. In an enlarged view (not shown) of the gas chromatograph, no peak was detected with a retention time of 15 minutes 00 seconds to 15 minutes 15 seconds derived from n-hexadecane.

TABLE D1

Butadiene Content

| Ethanol | | Butadiene Content (%) |
| --- | --- | --- |
| Ex. D1 | Derived from synthetic gas | 61.2 |
| Comp. Ex. D1 | Derived from fossil fuel | 57.2 |
| Comp. Ex. D2 | Derived from saccharification and fermentation | 57.5 |

As shown in Table D1, it has been found that ethanol produced using the gas discharged after burning general waste in a waste incineration facility has higher conversion efficiency to butadiene than ethanol derived from conventional fossil fuels or ethanol derived from saccharification fermentation from plants.

Example D2

(Production of Ethyl Benzoate)
Using the same ethanol as that used in Example D1, ethyl benzoate was manufactured in the same manner as in Example B, followed by component analysis using a gas chromatography apparatus to determine the amount of ethyl benzoate synthesis.

Comparative Example D3

Ethyl benzoate was manufactured and quantified in the same manner as in Example D2, except that ethanol derived from petrochemicals used in Comparative Example D1 was used. The analytical results were as shown in Table D2.

Comparative Example D4

Ethyl benzoate was manufactured and quantified in the same manner as in Example D2 except that ethanol derived from petrochemicals used in Comparative Example D2 was used. The analytical results were as shown in Table D2.

TABLE D2

Ethyl Benzoate Content

| Ethanol | | Ethyl Benzoate Content (%) |
| --- | --- | --- |
| Ex. D1 | Derived from synthetic gas | 94.4 |
| Comp. Ex. D1 | Derived from fossil fuel | 93.2 |
| Comp. Ex. D2 | Derived from saccharification and fermentation | 93.4 |

As shown in Table D2, it has been found that ethanol produced using the gas discharged after burning general waste in a waste incineration facility has a higher conversion efficiency to ethyl benzoate than ethanol derived from conventional fossil fuels or ethanol derived from saccharification fermentation from plants.

Example D3

The combustion efficiency of ethanol was quantified using the same ethanol as that used in Example D1. The fuel efficiency was quantified by adding 30 g of ethanol to a heat-resistant container of 60 mm in length×60 mm in width×30 mm in height under non-heating conditions, igniting, measuring the oxygen reduction until complete combustion in a cone calorimeter (manufactured by FTT), and calculating the total heat generation based on the oxygen reduction. The quantitative results were as shown in Table D3.

Comparative Example D5

The combustion efficiency of ethanol was quantified in the same manner as in Example D3 except that ethanol used in Comparative Example D1 was used. The quantitative results were as shown in Table D3.

Comparative Example D6

The combustion efficiency of ethanol was quantified in the same manner as in Example D3 except that ethanol used in Comparative Example D2 was used. The quantitative results were as shown in Table D3.

TABLE D3

| | Combustion Efficiency | |
| --- | --- | --- |
| | Ethanol | Combustion Efficiency (kw/kg) |
| Ex. D1 | Derived from synthetic gas | 7.78 |
| Comp. Ex. D1 | Derived from fossil fuel | 7.54 |
| Comp. Ex. D2 | Derived from saccharification and fermentation | 7.57 |

As shown in Tables A3-D3, it has been found that ethanol produced using gas discharged after burning general waste in a waste incineration facility has higher combustion efficiency than ethanol derived from conventional fossil fuels or ethanol derived from saccharification and fermentation from plants.

The invention claimed is:

1. A method for manufacturing ethanol, comprising:
  a step of converting a carbon source derived from waste by combustion and/or partial combustion into a synthetic gas comprising carbon monoxide and hydrogen;
  a step of purifying the synthetic gas;
  a microbial fermentation step of supplying the synthetic gas comprising carbon monoxide and hydrogen to a microbial fermentation tank to obtain an ethanol-containing liquid by microbial fermentation;
  a separation step of separating the ethanol-containing liquid into a liquid or solid component containing microorganisms and a gas component containing ethanol;
  a liquefaction step of condensing and liquefying the gas component;
  a purification step of purifying ethanol from the liquid obtained in the liquefaction step;
  wherein the purified ethanol is characterized in that the retention time has at least one peak selected from the group consisting of the following (A) to (D) in gas chromatography measured by gas chromatograph mass spectrometry (GC/MS):
    (A) a peak of 5 minutes 25 seconds to 5 minutes 35 seconds and two peaks of 2 minutes 55 seconds to 3 minutes 5 seconds;
    (B) a peak of 12 minutes 30 seconds to 12 minutes 40 seconds;
    (C) a peak of 6 minutes 36 seconds to 6 minutes 45 seconds; and
    (D) a peak of 15 minutes 00 seconds to 15 minutes 15 seconds.

2. The method according to claim 1, wherein the retention time in the gas chromatography further has a peak of 5 minutes 30 seconds to 5 minutes 35 seconds in addition to the peak of (A).

3. The method according to claim 1, wherein the peak of (B) is derived from n-tetradecane.

4. The method according to claim 3, wherein the concentration of n-tetradecane is 0.01 mg/L to 1.0 mg/L.

5. The method according to claim 1, wherein the peak of (C) is derived from n-decane.

6. The method according to claim 5, wherein the concentration of n-decane is between 0.01 mg/L and 1.0 mg/L.

7. The method according to claim 1, wherein the peak of (D) is derived from n-hexadecane.

8. The method according to claim 7, wherein the concentration of n-hexadecane is 0.01 mg/L to 1.0 mg/L.

9. A method for manufacturing ethanol, comprising:
  a step of converting a carbon source derived from waste by combustion and/or partial combustion into a synthetic gas comprising carbon monoxide and hydrogen;
  a microbial fermentation step of supplying the synthetic gas comprising carbon monoxide and hydrogen to a microbial fermentation tank to obtain an ethanol-containing liquid by microbial fermentation;
  a separation step of separating the ethanol-containing liquid into a liquid or solid component containing microorganisms and a gas component containing ethanol;
  a liquefaction step of condensing and liquefying the gas component;
  a purification step of purifying ethanol from the liquid obtained in the liquefaction step;
  wherein the purified ethanol is characterized in that the retention time has at least one peak selected from the group consisting of the following (A) to (D) in gas chromatography measured by gas chromatograph mass spectrometry (GC/MS):
    (A) a peak of 5 minutes 25 seconds to 5 minutes 35 seconds and two peaks of 2 minutes 55 seconds to 3 minutes 5 seconds;
    (B) a peak of 12 minutes 30 seconds to 12 minutes 40 seconds;
    (C) a peak of 6 minutes 36 seconds to 6 minutes 45 seconds; and
    (D) a peak of 15 minutes 00 seconds to 15 minutes 15 seconds;
  wherein the purified ethanol is further characterized by at least one of the following:
    (a) the retention time in the gas chromatography further has a peak of 5 minutes 30 seconds to 5 minutes 35 seconds in addition to the peak of (A);
    (b) the peak of (B) is derived from n-tetradecane;
    (c) the peak of (C) is derived from n-decane; or
    (d) the peak of (D) is derived from n-hexadecane.

10. The method according to claim 9, wherein the peak of (B) is derived from n-tetradecane and the concentration of n-tetradecane is 0.02 mg/L to 0.5 mg/L.

11. The method according to claim 10, wherein the concentration of n-tetradecane is 0.03 mg/L to 0.2 mg/L.

12. The method according to claim 11, wherein the concentration of n-tetradecane is 0.05 mg/L to 0.1 mg/L.

13. The method according to claim 9, wherein the peak of (C) is derived from n-decane and the concentration of n-decane is between 0.02 mg/L and 0.5 mg/L.

14. The method according to claim 13, wherein the concentration of n-decane is between 0.03 mg/L and 0.2 mg/L.

15. The method according to claim 14, wherein the concentration of n-decane is 0.05 mg/L to 0.1 mg/L.

16. The method according to claim 9, wherein the peak of (D) is derived from n-hexadecane and the concentration of n-hexadecane is 0.02 mg/L to 0.5 mg/L.

17. The method according to claim 16, wherein the concentration of n-hexadecane is 0.03 mg/L to 0.2 mg/L.

18. The method according to claim 17, wherein the concentration of n-hexadecane is 0.05 mg/L to 0.1 mg/L.

* * * * *